(12) United States Patent
Feith et al.

(10) Patent No.: US 11,819,654 B2
(45) Date of Patent: Nov. 21, 2023

(54) CASTELLATED CHECK VALVES

(71) Applicant: CareFusion 303, Inc., San Diego, CA (US)

(72) Inventors: Raymond P. Feith, Chino Hills, CA (US); Eugene Mason, La Habra Heights, CA (US); Christian Crew, Raleigh, NC (US)

(73) Assignee: CAREFUSION 303, INC., San Diego, CA (US)

( * ) Notice: Subject to any disclaimer, the term of this patent is extended or adjusted under 35 U.S.C. 154(b) by 48 days.

(21) Appl. No.: 16/292,223

(22) Filed: Mar. 4, 2019

(65) Prior Publication Data
US 2020/0282199 A1    Sep. 10, 2020

(51) Int. Cl.
*A61M 39/24* (2006.01)
*F16K 15/14* (2006.01)

(52) U.S. Cl.
CPC ..... *A61M 39/24* (2013.01); *A61M 2039/2406* (2013.01); *A61M 2039/2433* (2013.01); *F16K 15/144* (2013.01)

(58) Field of Classification Search
CPC .......... A61M 39/24; A61M 2039/2406; A61M 2039/2433; A61M 2039/2446; A61M 39/22; A61M 2039/2453; A61M 2039/246; A61M 2039/2466; A61M 2039/2493; A61M 2205/0216; A61M 2205/33; A61M 2205/3331; A61M 2205/3334;
(Continued)

(56) References Cited

U.S. PATENT DOCUMENTS 4,103,686 A * 8/1978 LeFevre ............... A61M 5/172
604/249
4,141,379 A   2/1979 Manske
(Continued)

FOREIGN PATENT DOCUMENTS

CH     524090 A  * 6/1972   ........... F16K 15/141
CH     705428 A2   1/2013
(Continued)

OTHER PUBLICATIONS

International Search Report and Written Opinion for Application No. PCT/US2020/020841, dated Jun. 17, 2020, 15 pages.
(Continued)

*Primary Examiner* — Kevin C Sirmons
*Assistant Examiner* — Avery Smale
(74) *Attorney, Agent, or Firm* — Morgan Lewis & Bockius LLP

(57) ABSTRACT

A check valve includes an upper housing defining an inlet of the check valve, a lower housing defining an outlet of the check valve, and a cavity interposed between and defined by the upper and lower housings for fluidly connecting the inlet and the outlet. The check valve further includes a valve member mounted in the cavity to selectively permit fluid flow in a first direction, and prevent fluid backflow in a second direction opposite to the first direction. The valve member includes a valve body and a valve stem portion extending axially through a central axis of the valve body. The valve member may further include a plurality of feet disposed about and extending longitudinally from an outer circumferential perimeter of the valve body.

12 Claims, 16 Drawing Sheets

(58) Field of Classification Search
CPC .. A61M 2205/3337; A61M 2205/3341; A61M 2205/75; A61M 5/168; A61M 5/16804; A61M 5/16813; A61M 5/16877; A61M 5/16881; F16K 15/144; F16K 15/00; F16K 15/14; F16K 15/141; F16K 15/147; F16K 15/148

See application file for complete search history.

(56) References Cited

U.S. PATENT DOCUMENTS

| | | | | |
|---|---|---|---|---|
| 4,244,378 | A | * | 1/1981 | Brignola ............... A61J 1/2089 600/579 |
| 4,332,249 | A | | 6/1982 | Joslin |
| 4,781,674 | A | * | 11/1988 | Redmond ........... A61M 27/006 137/854 |
| 4,890,640 | A | | 1/1990 | King |
| 4,904,236 | A | * | 2/1990 | Redmond ........... A61M 27/006 604/9 |
| 5,860,449 | A | | 1/1999 | Schulte |
| 5,992,462 | A | * | 11/1999 | Atkinson ............... A61M 39/24 137/515.5 |
| 6,904,929 | B2 | | 6/2005 | Ruschke |
| 7,997,293 | B2 | | 8/2011 | Ruschke |
| 8,162,006 | B2 | | 4/2012 | Guala |
| 8,911,621 | B2 | | 12/2014 | Lippert et al. |
| 9,352,086 | B2 | | 5/2016 | Guala |
| 9,421,354 | B2 | | 8/2016 | Carmody et al. |
| 9,504,783 | B2 | | 11/2016 | Peters |
| 2004/0188541 | A1 | | 9/2004 | Maruyama |
| 2010/0215522 | A1 | | 8/2010 | Kawamura et al. |
| 2012/0004623 | A1 | | 1/2012 | Tumminaro et al. |
| 2012/0256114 | A1 | * | 10/2012 | Buiser ................... F16K 15/144 251/331 |
| 2015/0352349 | A1 | * | 12/2015 | Carmody ............... A61M 39/22 137/544 |
| 2016/0129181 | A1 | * | 5/2016 | Mijers ................... A61M 39/24 604/247 |

FOREIGN PATENT DOCUMENTS

| | | |
|---|---|---|
| DE | 1106568 B | 5/1961 |
| FR | 2119367 A5 | 8/1972 |
| WO | WO-2007083892 A1 | 7/2007 |

OTHER PUBLICATIONS

European Office Action for Application No. 20716037.5, dated Jul. 5, 2023, 5 pages.

Indian Office Action for Application No. 202117040994, dated Sep. 4, 2023, 7 pages.

* cited by examiner

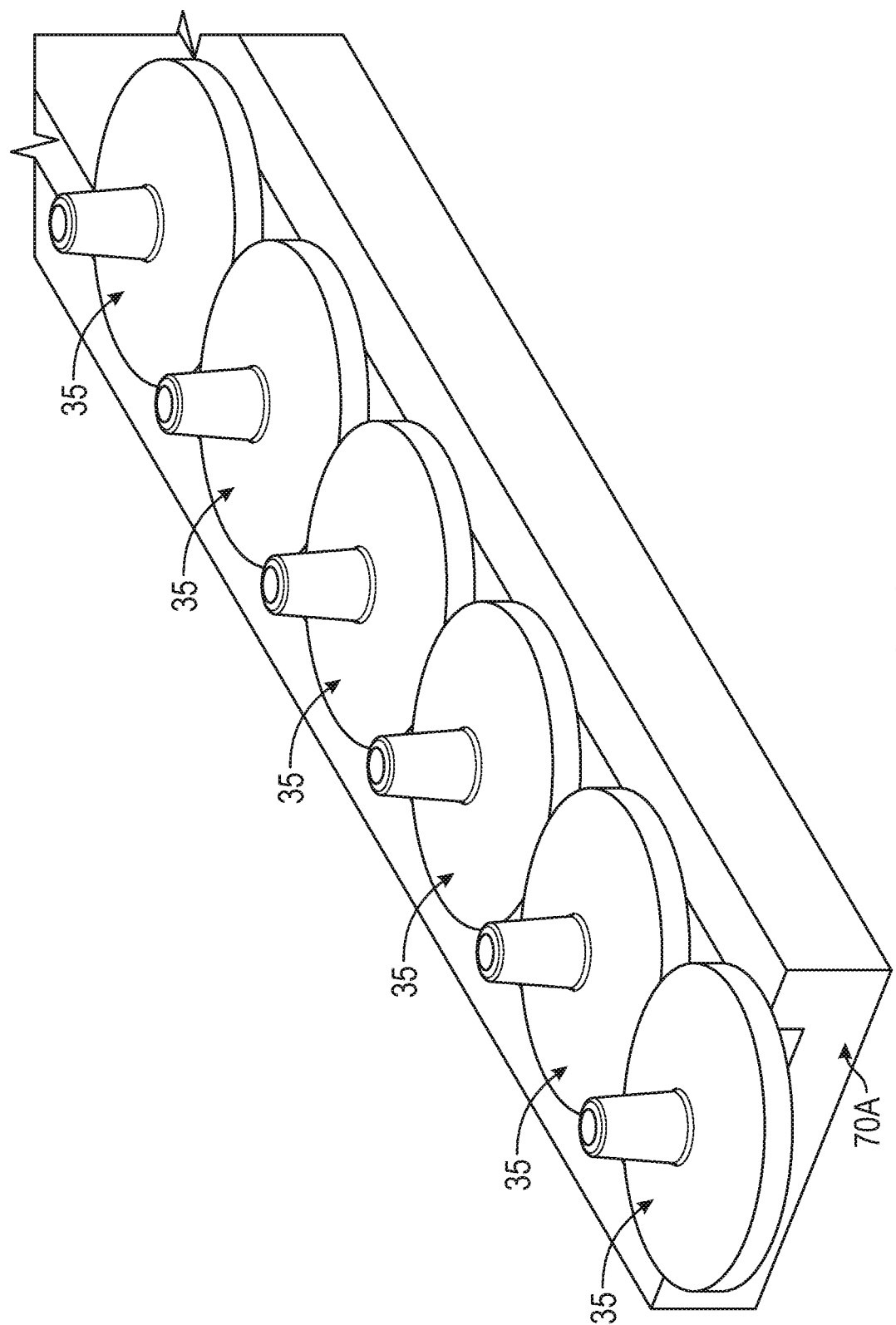

CASTELLATED CHECK VALVES

TECHNICAL FIELD

The present disclosure generally relates to check valves, and more particularly to valve members of check valves having geometries capable of minimizing sticking together of the valve members during bulk packing or during assembly of the check valves.

BACKGROUND

Patients are commonly injected with IV solutions that are initially provided in an IV reservoir (a bottle or bag) and dripped into the vein of the patient through an IV line. Typically, an injection port is provided along the IV line and adapted to function with a syringe to permit an injectate to be added to the IV solution. A check valve is also commonly included in the IV line to permit fluid flow only in the direction of the patient. This ensures that the injectate flows downstream toward the patient, not upstream toward the IV reservoir.

Conventional check valves utilize disc-shaped valve members that are generally flat and usually made of silicone which is naturally sticky. This geometry allows for the valve members to stick together (during bulk packing) thereby causing a condition known as "shingling" which makes automated assembly of the conventional check valves difficult.

SUMMARY

The present disclosure generally relates to check valves, and more particularly to valve members of check valves having geometries capable of minimizing sticking together of the valve members during bulk packing or during assembly of the check valves.

In accordance with various embodiments of the present disclosure, a check valve includes an upper housing, a lower housing, a cavity interposed between and defined by the upper and lower housings, and a valve member mounted in the cavity to selectively permit fluid flow in a first direction, and prevent fluid backflow in a second direction opposite to the first direction. The upper housing defines an inlet of the check valve and the lower housing defines an outlet of the check valve. The cavity fluidly connects the inlet and the outlet. The valve member includes a valve body and a valve stem portion extending axially through a central axis of the valve body.

In accordance with various embodiments of the present disclosure, a check valve includes an upper housing defining an inlet of the check valve, a lower housing axially coupled to the upper housing and comprising an outlet of the check valve, and a cavity interposed between and defined by the upper and lower housings for fluidly connecting the inlet and the outlet. The check valve further includes a flexible valve member mounted in the cavity to selectively permit fluid flow in a first direction, and prevent fluid backflow in a second direction opposite to the first direction. The flexible valve member includes a body having a plurality of longitudinally extending feet disposed about an outer circumferential perimeter of the body.

In accordance with various embodiments of the present disclosure, a flexible valve member includes a valve body, and a plurality of feet disposed about and extending longitudinally from an outer circumferential perimeter of the valve body.

It is to be understood that both the foregoing general description and the following detailed description are exemplary and explanatory and are intended to provide further explanation of the subject technology as claimed. It is also to be understood that other aspects may be utilized, and changes may be made without departing from the scope of the subject technology

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

FIG. 1C illustrates an assembly line of the valve member of the check valve of FIG. 1B in accordance with some embodiments.

DETAILED DESCRIPTION

Figure 1A:
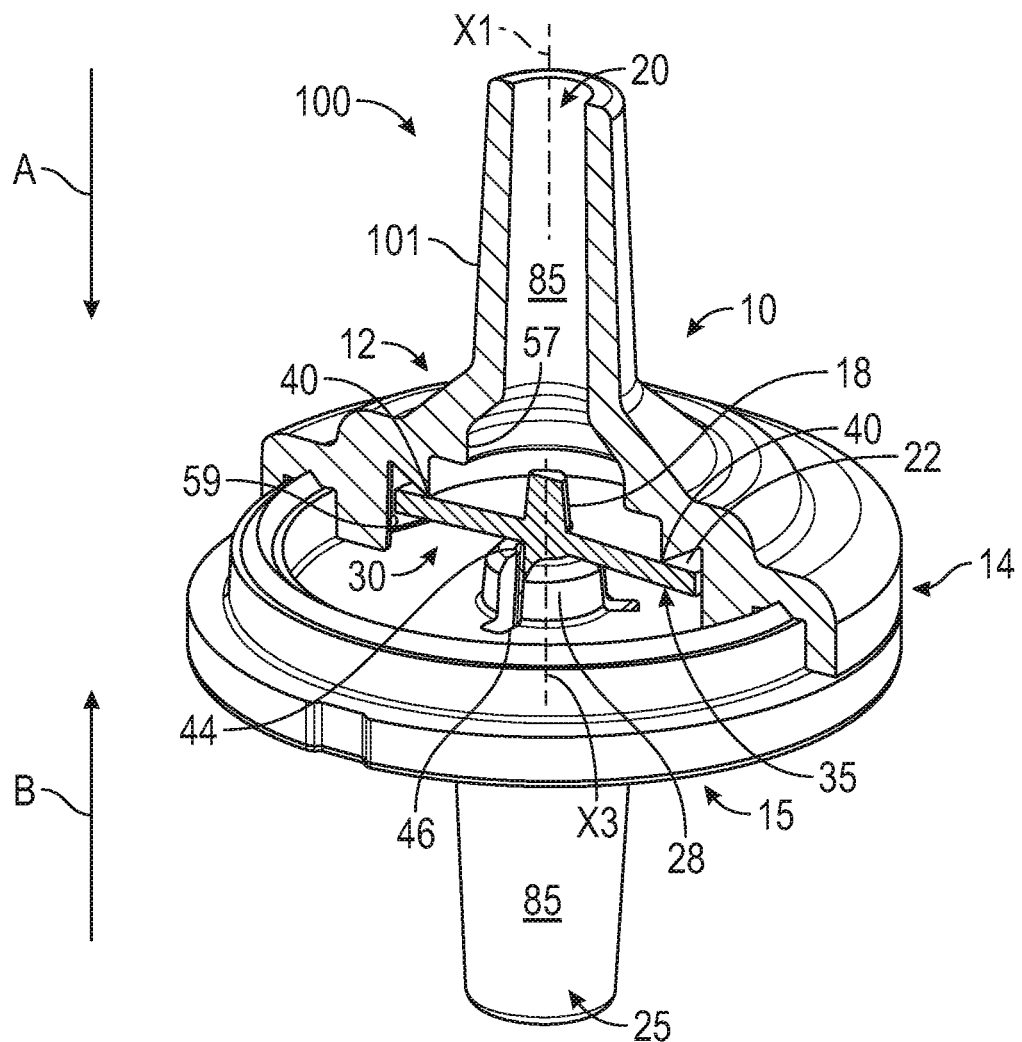
FIG. 1A is a perspective view of a check valve, in accordance with some embodiments of the present disclosure.

The detailed description set forth below describes various configurations of the subject technology and is not intended to represent the only configurations in which the subject technology may be practiced. The detailed description includes specific details for the purpose of providing a thorough understanding of the subject technology. Accordingly, dimensions may be provided in regard to certain aspects as non-limiting examples. However, it will be apparent to those skilled in the art that the subject technology may be practiced without these specific details. In some instances, well-known structures and components are shown in block diagram form in order to avoid obscuring the concepts of the subject technology.

It is to be understood that the present disclosure includes examples of the subject technology and does not limit the scope of the appended claims. Various aspects of the subject technology will now be disclosed according to particular but non-limiting examples. Various embodiments described in the present disclosure may be carried out in different ways and variations, and in accordance with a desired application or implementation.

The present description relates in general to check valves, and more particularly, for example and without limitation, to more particularly to valve members of check valves having geometries capable of minimizing sticking together of valve members during bulk packing or during assembly of the check valves.

In accordance with some embodiments, the valve member may include a valve body and a valve stem portion extending axially through a central axis of the valve body. The valve members of the various embodiments described herein are advantageous in that the valve body and the valve stem portion may define a "jack" shape geometry that will reduce the exposed surface area available for sticking of the valve members during assembly. In particular, the presence of the valve stem portion limits the exposed surface area of the valve bodies available for sticking or "shingling." In some embodiments, the exposed surface area of the valve members available for sticking is reduced by up to 69%. The valve members can then be fed along an assembly line or track with reduced surface area for sticking and/or friction.

In accordance with some embodiments, the valve member either including or excluding the stem portion may additionally include plurality of feet at an outer circumferential perimeter of the valve body. The feet may each extend longitudinally from the outer circumferential perimeter of the valve body. The feet may be spaced apart from each other so as to form a castle-like shape around the perimeter of the valve body, and thus may be referred to as castellated feet. As depicted, the castellated feet may be oriented substantially perpendicularly with respect to the outer circumferential perimeter of the valve body. Benefits are realized in the geometry of the valve members with the castellated feet in that the castellated feet further prevent or obstruct contacting of the upper and/or lower surfaces of the valve bodies during bulk packing, assembly and/or transportation. In particular, since the upper surface of each of the castellated feet protrudes and is thus raised above the upper surface of the valve body, contacting and sticking together of the exposed surface areas of the upper surfaces of the valve body is limited. Similarly, since the lower surface of each of the castellated feet protrudes below the lower surface of the valve body, contacting and sticking together of the exposed surface areas of the lower surfaces of the valve body is limited. Additional benefits are realized in that due to the longitudinally protruding structure of the castellated feet, the valve member is capable of being maintained concentrically in a cavity of the check valve when the valve experiences a back pressure condition. Valves are symmetrical and can be assembled on either side.

Figure 1B:
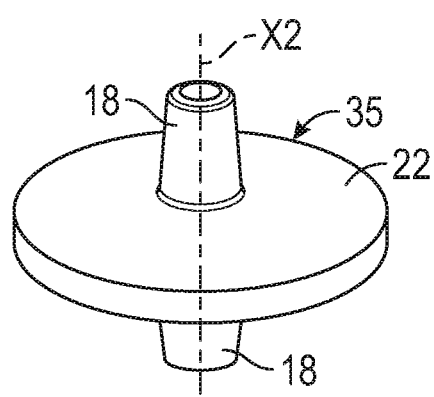
FIG. 1B is a perspective view of a valve member of the check valve of FIG. 1A, in accordance with some embodiments of the present disclosure.

FIG. 1A is a perspective view of a check valve 100, in accordance with some embodiments of the present disclosure. FIG. 1B is a perspective view of a valve member 35 of the check valve of FIG. 1A, in accordance with some embodiments of the present disclosure. FIG. 1C illustrates an assembly line of the valve member 35 of the check valve 100 of FIG. 1B in accordance with some embodiments. As depicted, a top portion of the check valve 100 (i.e., an upper housing 10) is displayed in cross-sectional view to more clearly illustrate some of the features of the check valve 100. Referring to FIG. 1, the check valve 100 includes an axially extending body 101 defining a central longitudinal axis X1. The body 101 may be a generally cylindrical (or tubular) structure and may include an upper housing 10 and a lower housing 15. The upper housing 10 may include a first end portion 12 and an axially opposite second end portion 14. As illustrated, a radial extent of the upper housing 10 at the second end portion 14 may be greater than the radial extent thereof at the first end portion 12. The lower housing 15 may include an upstream internal surface 52, and the second end portion 14 and the upstream internal surface 52 of the lower housing 15 may axially contact each other to co-operatively form a cavity 30 of the check valve 100.

The upper housing 10 may include an inlet 20 of the check valve 100 at the first end 12, and the lower housing 15 may include an outlet 25 of the check valve 100. The body 101 may define an internal flow passage 85 axially extending between the inlet 20 and the outlet 25 and in fluid communication therewith. As is understood, the check valve 100 may permit fluid to flow from the inlet 20 to the outlet 25 (as indicated by arrow A), and minimize, or otherwise limit, fluid flow from the outlet 25 to the inlet 20 (as indicated by arrow B). As depicted, the upper housing 10 and the lower housing 15 may define the cavity 30 for fluidly connecting the inlet 20 and the outlet 25. In the depicted embodiments the flexible valve member 35 may be mounted in the cavity 30 to selectively permit fluid flow in the first direction (indicated by arrow A), and prevent fluid backflow (reverse flow) in the second direction opposite to the first direction (indicated by arrow B).

In accordance with some embodiments, the valve member 35 may have a valve body 22 and a valve stem portion 18 extending axially through a central axis X2 of the valve body 22. The valve body 22 may be in the form of a disc or any other circular plate. As depicted, the valve member 35 may be mounted on a support portion 28 of the lower housing 14. In particular, the support portion 28 may include a central aperture 44 and a plurality of axially extending slots 46 through which fluid flowing from the inlet 20 and into the cavity 30 may enter the outlet 25 in an open state of the check valve 100. As depicted, the valve stem portion 18 of the valve member 35 may be mounted in the central aperture 44 of the support portion. The aforementioned configuration of the valve member 35 may provide several manufacturing and assembly advantages. A common issue experienced during packaging, transportation and assembly of the check valve is that when conventional valve members (e.g., disc-type check valve members) are packaged in bulk and/or transported on a conveyance line, the valve members are prone to shingling. In particular, since conventional disc-type valve members are generally flat and made of silicone which is naturally sticky, this geometry allows for the conventional disc-type valve members to stick together (during bulk packing), thereby causing the "shingling". This makes automated assembly difficult. The valve member 35 of the various embodiments described herein is advantageous in that the valve body 22 and the valve stem portion 18 may define a "jack" shape geometry of the valve member 35 that will reduce the exposed surface area available for sticking of the valve members 35 during assembly. In particular, the presence of stem portion 18 limits the exposed surface area of the bodies 22 available for sticking or shingling. The probability for sticking of the valve members to occur is thus much lower since the stem portions will keep surfaces of the bodies apart at least in part. In some embodiments, the exposed surface area of the valve members 35 available for sticking is reduced by up to 69%. As illustrated in FIG. 1C, the valve members 35 can now be fed along a track 70A with reduced surface area for sticking and/or friction. Additional benefits are realized in that since the valve members 35 will be concentrically disposed in the cavity 30 of the check valve 100, peripheral circumferential edges of the valve member 35 are prevented from contacting an internal surface, e.g., a downstream internal surface 59 (described in further detail below) of the upper housing 10, which could hold the valve open. Furthermore, because the valve member 35 is symmetrically shaped it can be assembled on either side thereof.

Referring back to FIG. 1A, the support portion 28 may be centrally disposed in the cavity 30, and a central axis X3 of the support portion 28 may be coaxially aligned with the central longitudinal axis X1 of the body 101. The support portion 28 may be coupled to, integrally formed with, or otherwise protrude from the upstream internal surface 52 of the lower housing 15, and extend into the cavity 30. As discussed in further detail below, the cavity 30 may form a part of the internal flow passage 85, or may be otherwise fluidly communicated with the internal flow passage 85 and therefore, fluid flowing from the inlet 20 to the outlet 25 may flow via the cavity 30.

Figure 2A:
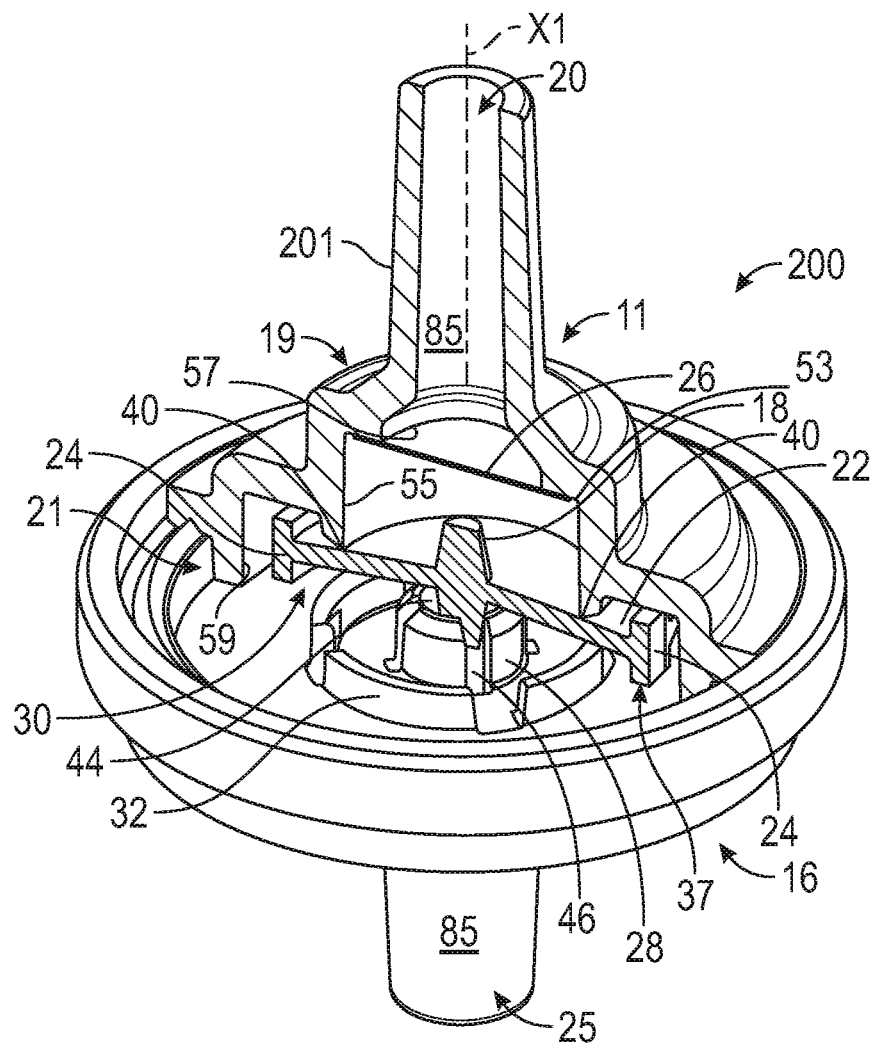
FIG. 2A is a perspective view of a check valve, in accordance with some embodiments of the present disclosure.
Figure 2B:
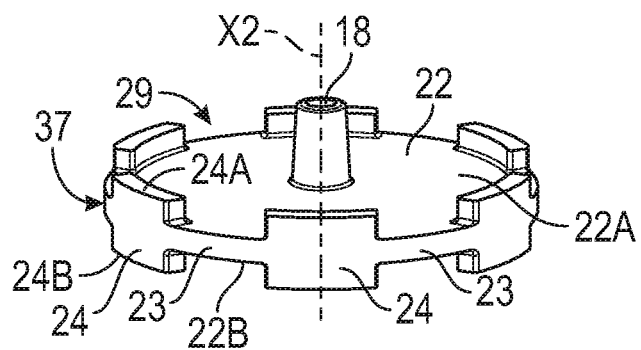
FIG. 2B is a perspective view of a valve member of the check valve of FIG. 2A, in accordance with some embodiments of the present disclosure.
Figure 2C:
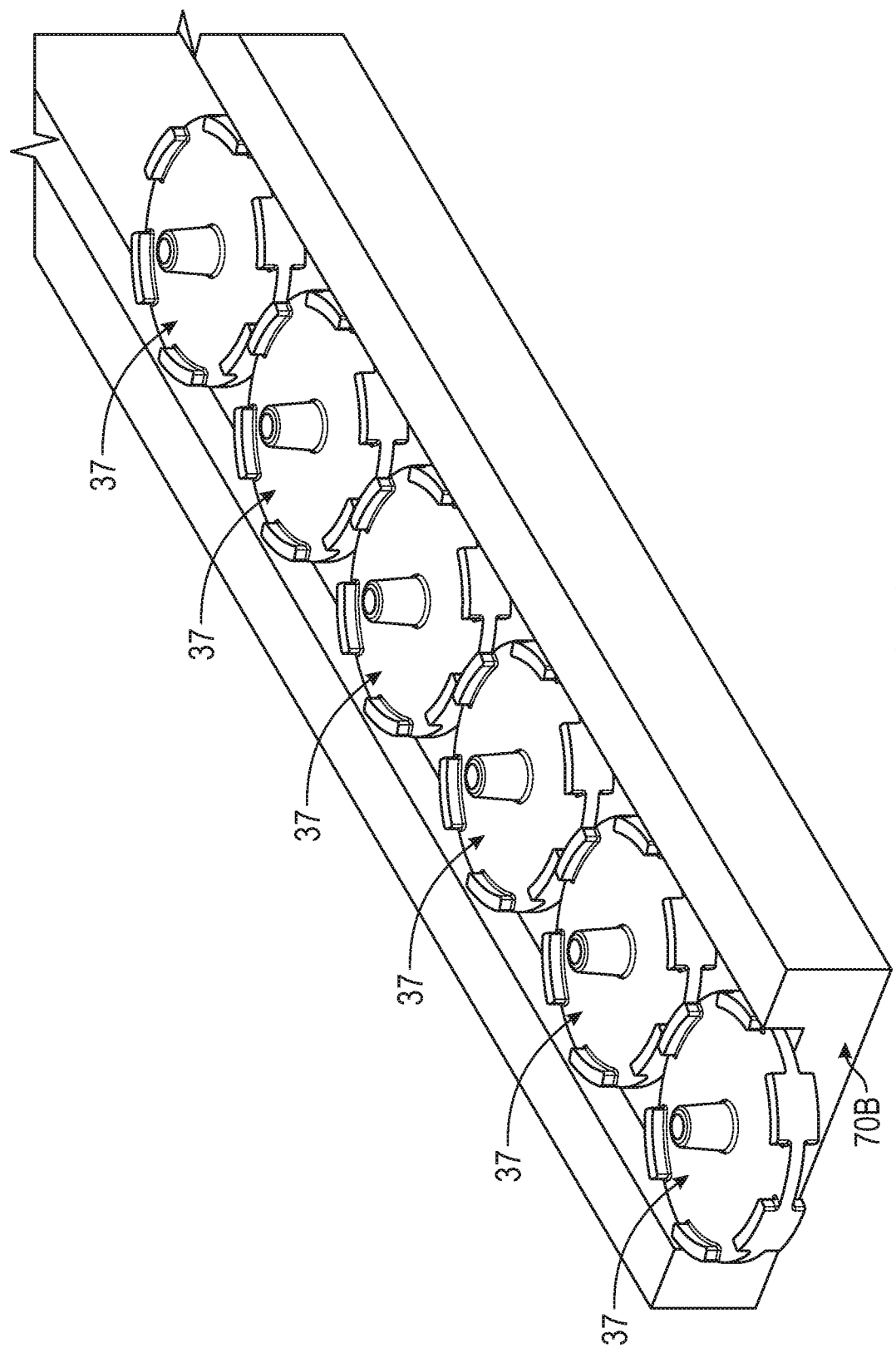
FIG. 2C illustrates an assembly line of the valve member of the check valve of FIG. 2B in accordance with some embodiments.

FIG. 2A is a perspective view of a check valve 200, in accordance with some embodiments of the present disclosure. FIG. 2B is a perspective view of a valve member 37 of the check valve 200 of FIG. 2A, in accordance with some embodiments of the present disclosure. FIG. 2C illustrates an assembly line of the valve member 37 of the check valve 200 of FIG. 2B in accordance with some embodiments. As depicted, a top portion of the check valve 200 (i.e., an upper housing 11) is displayed in cross-sectional view to more clearly illustrate some of the features of the check valve 200. Referring to FIG. 2A, similar to the embodiments of FIG. 1A, the check valve 200 includes an axially extending body 201 defining a central longitudinal axis X1. The body 201 may be a generally cylindrical (or tubular) structure and may include an upper housing 11 and a lower housing 16. The upper housing 11 may include a first end portion 19 and an axially opposite second end portion 21. As illustrated, a radial extent of the upper housing 11 at the second end portion 21 may be greater than the radial extent thereof at the first end portion 19. The lower housing 16 may include an upstream internal surface 52, and the second end portion 21 and the upstream internal surface 52 of the lower housing 16 may axially contact each other to co-operatively form a cavity 30 of the check valve 200.

The upper housing 11 may include an inlet 20 of the check valve 200 at the first end 19, and the lower housing 16 may include an outlet 25 of the check valve 200. Similar to the embodiments of FIG. 1A, the body 201 may define an internal flow passage 85 axially extending between the inlet 20 and the outlet 25 and in fluid communication therewith. As is understood, the check valve 200 may permit fluid to flow from the inlet 20 to the outlet 25, and minimize or otherwise limit, fluid flow from the outlet 25 to the inlet 20. As depicted, the upper housing 11 and the lower housing 16 may define the cavity 30 for fluidly connecting the inlet 20 and the outlet 25. In the depicted embodiments the flexible valve member 37 may be mounted in the cavity 30 to selectively permit fluid flow from the inlet 20 to the outlet 25, and prevent fluid backflow (reverse flow) from the outlet 25 to the inlet 20.

In accordance with some embodiments, similar to the valve member 35, the valve member 37 may have a valve body 22 and a valve stem portion 18 extending axially through the central axis X2 of the valve body 22. In the depicted embodiments, the valve member 37 additionally has a plurality of feet 24 disposed along an outer circumferential perimeter 33 of the valve body 22. The feet 24 may each extend longitudinally from the outer circumferential perimeter 23 of the valve body 22. As depicted, the feet 24 may be oriented substantially perpendicularly with respect to the outer circumferential perimeter 23 of the valve body 22. In particular, the feet 24 may extend from and protrude substantially perpendicularly from an upper surface 22A and a lower surface 22B of the valve body 22. As such, an upper surface 24A of each of the feet 24 may be positioned or protrude a predetermined height above the upper surface 22A of the valve body 22. Similarly, a lower surface 24B of each of the feet 24 may be positioned or protrude a predetermined height below the lower surface 22B of the valve body 22. In some embodiments, the feet 24 may be spaced apart from each other at regular intervals. For example, the valve member 37 may have two or more feet 24 equally spaced apart from each other. In other embodiments. However, the feet 24 may be spaced apart from each other at irregular intervals. For example, a spacing between each of the feet may vary according to the desired application. In some embodiments, adjacent pairs of the feet 24 define a recessed flow portion 29 therebetween, and through which fluid entering the cavity 30 from the upper housing may flow into the lower housing.

As depicted, the feet 24 may have a polygonal shape, for example a rectangular, square or any other suitable polygonal shape. In other embodiments, the feet 24 may have a curved shape, for example a circular, an oval or oblong shape. The configuration of the valve member 37 with adjacent feet 24 interposed by respective recessed flow portions 29 may yield a structure resembling that of a castle. Thus, the feet 24 may be referred to herein as castellated feet 24. However, the various embodiments of the present disclosure are not limited the aforementioned configurations, and the shapes and spacing apart (i.e. the extent or size of the recessed flow portions 29) of the feet 24 from each other may be varied as desired.

Similar to the embodiments of FIG. 1A, the valve member 37 may be mounted on a support portion 28 of the lower housing 16. In particular, the support portion 28 may include a central aperture 44 and a plurality of axially extending slots 46 through which fluid flowing from the inlet 20 and into the cavity 30 may enter the outlet 25 in an open state of the check valve 200. As depicted, the valve stem portion 18 of the valve member 35 may be mounted in the central aperture 44 of the support portion 28. The aforementioned configuration of the valve member 37 may provide similar and additional manufacturing and assembly advantages as the valve member 35 of FIGS. 1A-1C. In particular, due to the valve member 37 also being configured with the valve stem portion 18, the common issues described above which are experienced during packaging, assembly, and transportation are minimized. The "jack" shape geometry of the valve member 37 reduces the exposed surface area available for sticking of the valve members 35 during assembly, thereby reducing the possibility of occurrence of "shingling" or sticking together of the surfaces of the valve bodies 22 during transportation or assembly.

In some embodiments, the exposed surface area of the valve members 37 available for sticking is reduced by up to 69%. As illustrated in FIG. 2C, the valve members 37 can now be fed along a track 70B with reduced surface area for sticking and/or friction. Benefits are realized in the geometry of the valve members 37 in that the castellated feet 24 further prevent or obstruct contacting of the upper and/or lower surfaces 22A, 22B of the valve bodies 22 during assembly and/or transportation. In particular, the configuration of the valve members 37 in which the upper surface 24A of each of the castellated feet 24 protrudes and is thus raised above the upper surface 22A of the valve body 22 further limits the exposed surface area of the lower surfaces 22A from contacting and sticking to each other. Similarly, the configuration of the valve members 37 in which the lower surface 24B of each of the castellated feet 24 protrudes below the lower surface 22B of the valve body 22 further limits the exposed surface area of the lower surfaces 22B from contacting and sticking to each other. Thus, the probability for sticking of the valve members 37 to occur is much lower than conventional valve members as the castellated feet 24 will keep surfaces of the bodies 22 apart at least in part. In some embodiments, the exposed surface area of the valve members 37 available for sticking is reduced by up to 69%. As can be appreciated, the degree of reduction of the exposed surface area of the valve members 37 that is available for sticking may vary accordingly based on the size and geometry of the castellated feet 24. Additional benefits are realized in that due to the longitudinally protruding structure of the castellated feet 24, the valve member 37 is capable of being maintained concentrically in the cavity 30 of the check valve 200 when the valve member 37 experiences a back pressure condition. Furthermore, because the valve member 37 is symmetrically shaped it can be assembled on either side thereof. In all other respects, the valve member 37 may be identical to the valve member 35 described above with respect to FIG. 1B.

In accordance with some embodiments, the check valve 200 may further include a filter member 26 coupled, attached or otherwise bonded to an internal surface, e.g., surface 55 of the upper housing 11. For example, the filter member 26 may be coupled, attached or otherwise bonded to a ledge 53 of the internal surface 55 through any appropriate methods including, but not limited to ultrasonic welding, heat sealing, insert molding, gluing or other attachment methods. The filter member 26 may be disposed upstream of, and spaced apart from the valve member 37. As such, when the valve member 37 is subjected to an excessive reverse flow (flow from the outlet 25 to the inlet 20) causing the valve member 37 to bow or deflect upwards, a gap remains between the filter member 26 and the valve member 37 to prevent the valve member 37 from stretching the filter member 26 past its elastic limit. Thus integrity of the filter member 26 is maintained even in the excessive backflow condition. The filter member 26 may be configured to restrict and minimize passage of undesirable matter in the fluid flowing through the check valve 200.

The filter member 26 may be formed of a porous material capable of preventing particulate matter of a particular size from passing through and potentially reaching and causing failure of the valve member 37. For example, the filter member 26 may be formed of a porous plastic material. Alternatively, the filter member 26 may be made of a non-woven cast material, a cork material, or any other porous fabric or material. The filter member 26 may be formed with a plurality of small holes or it may be woven, to provide pores of about 20 to 200 microns in size. In some embodiments, filter member 26 may be a flexible material such as a metal or polymeric material. In some embodiments, the filter member 40 may be formed of a material capable of withstanding or filtering flow rates of between 3 to 8 liters per hour. Additionally, the filter member 26 may be formed of a porous material capable of withstanding backpressures resulting from reverse flow of up to 200 KPa. Advantageously, the latter configuration may minimize the possibility of the filter member 26 collapsing under the backpressure resulting from reverse fluid flow.

Figure 3:
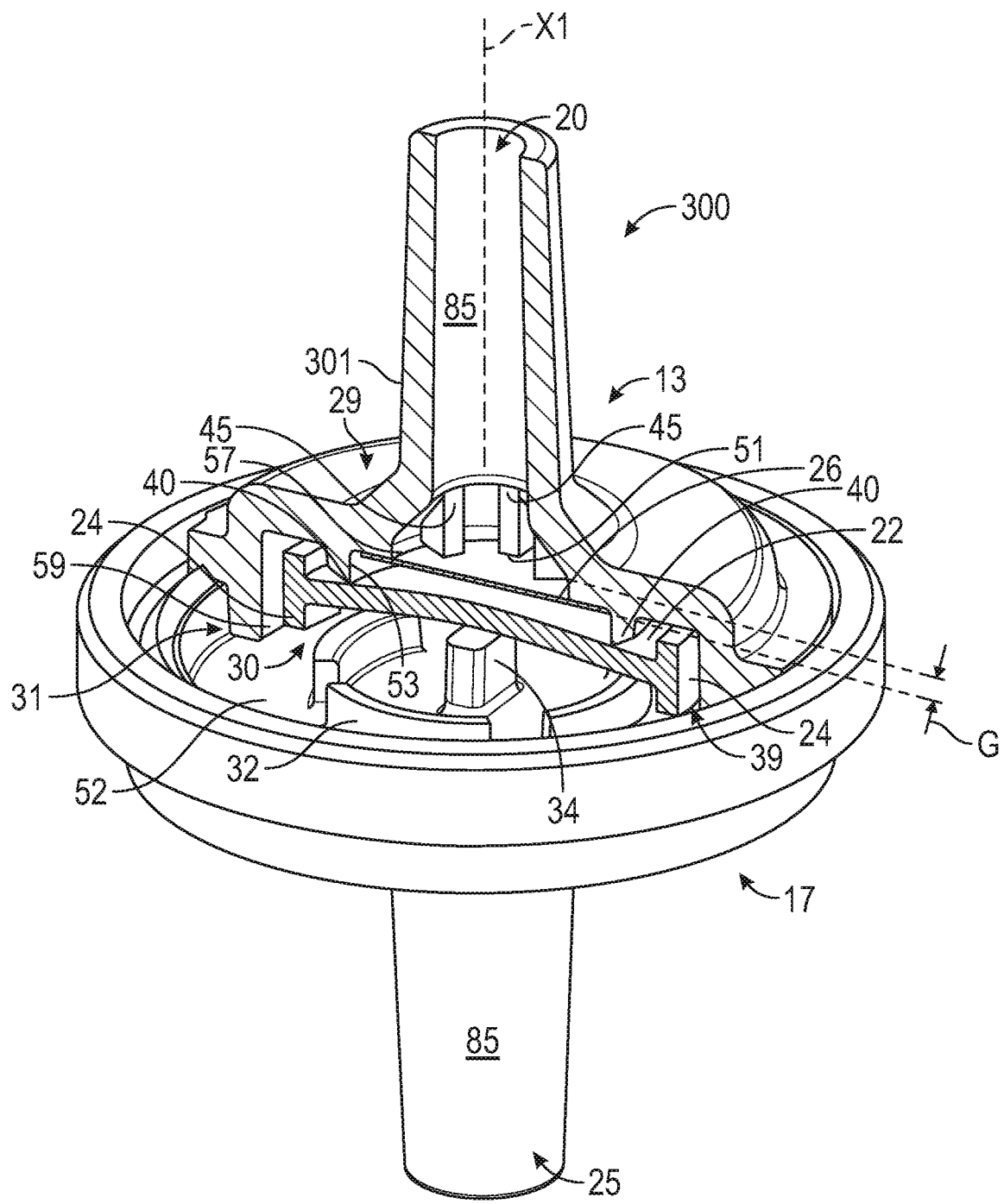
FIG. 3 is a perspective view of a check valve, in accordance with some embodiments of the present disclosure.
Figure 4A:
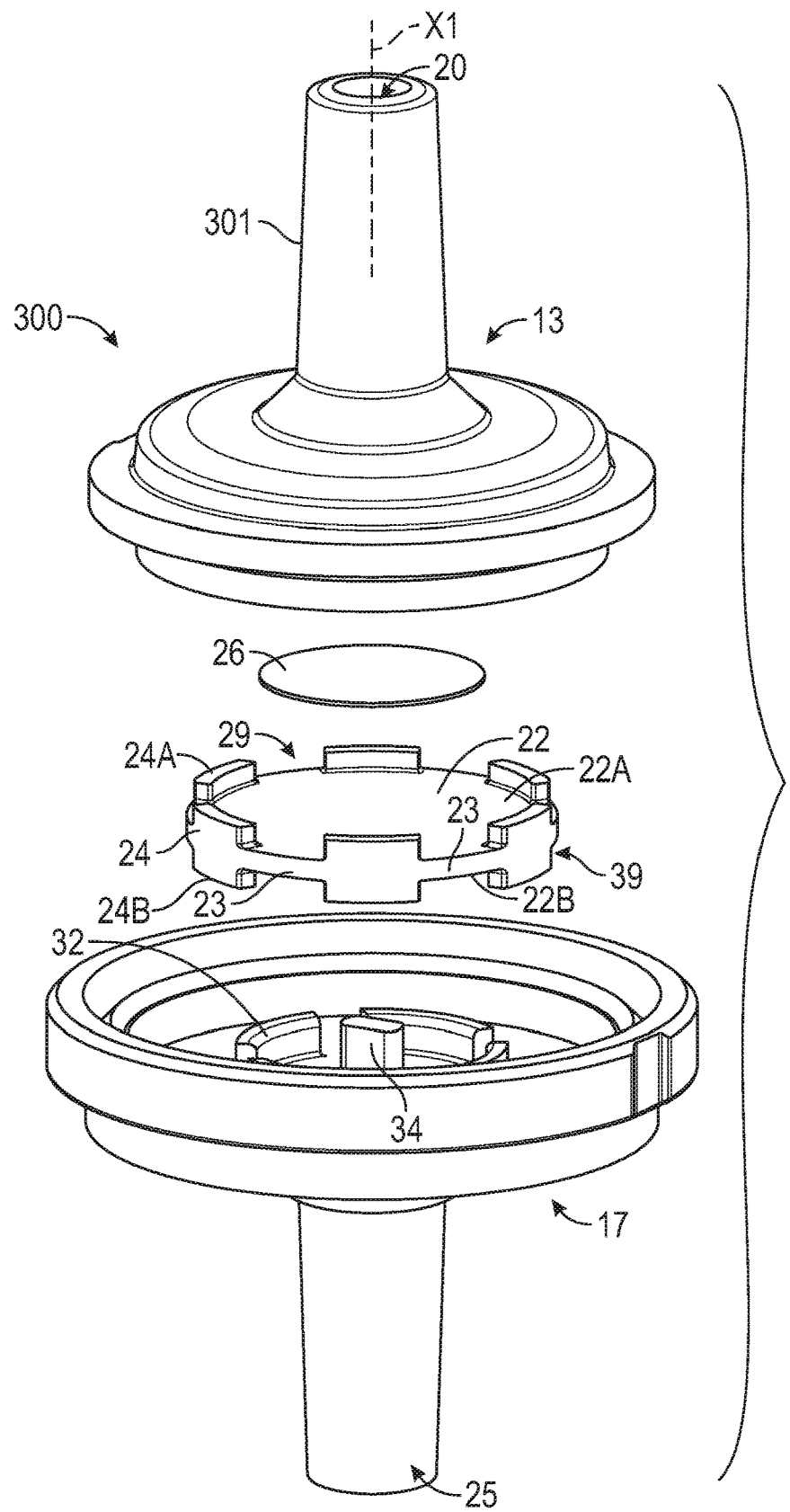
FIG. 4A is an exploded perspective view of the check valve of FIG. 3, in accordance with some embodiments of the present disclosure.
Figure 4B:
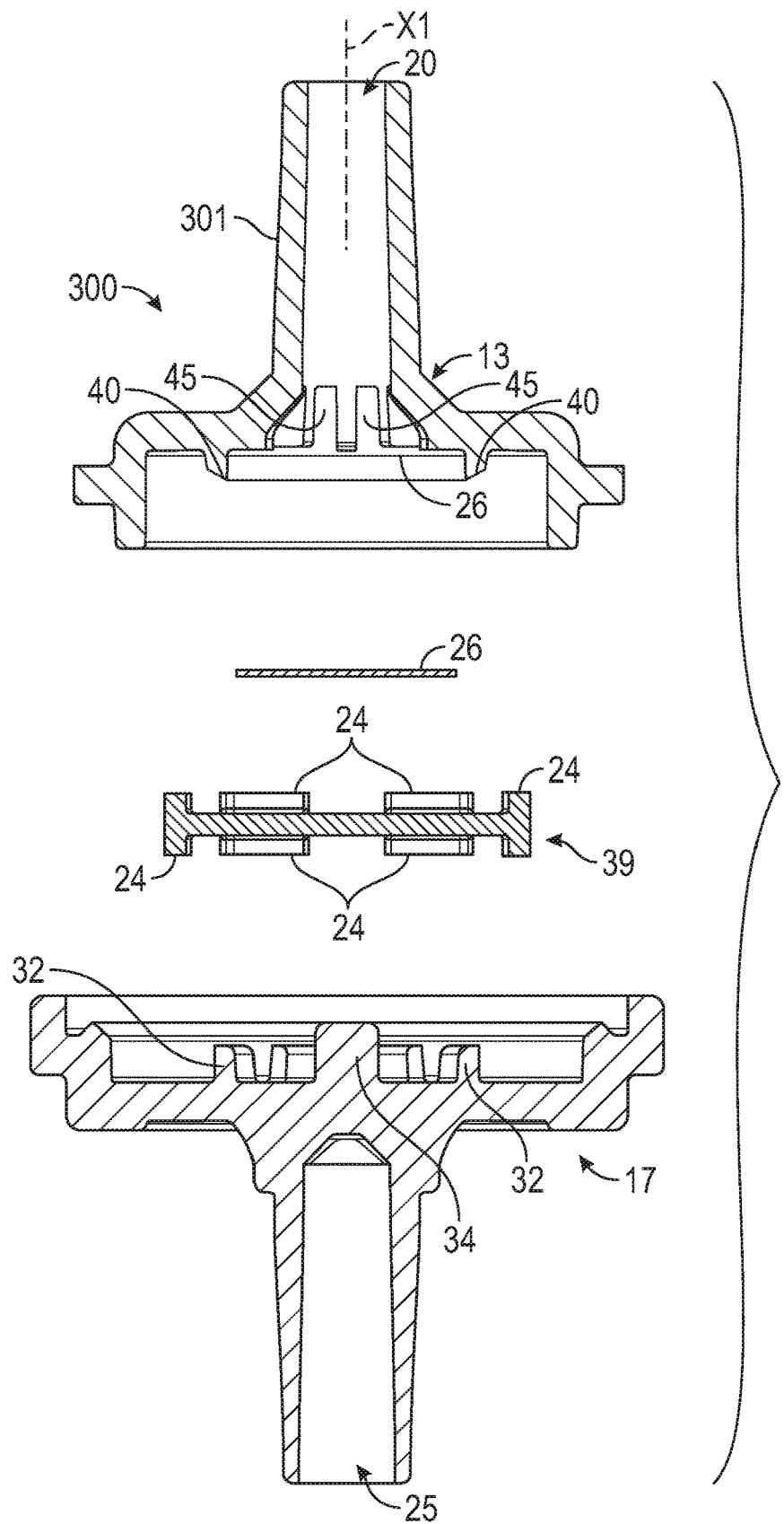
FIG. 4B is an exploded cross-sectional view of the check valve of FIG. 3, in accordance with some embodiments of the present disclosure.
Figure 4C:
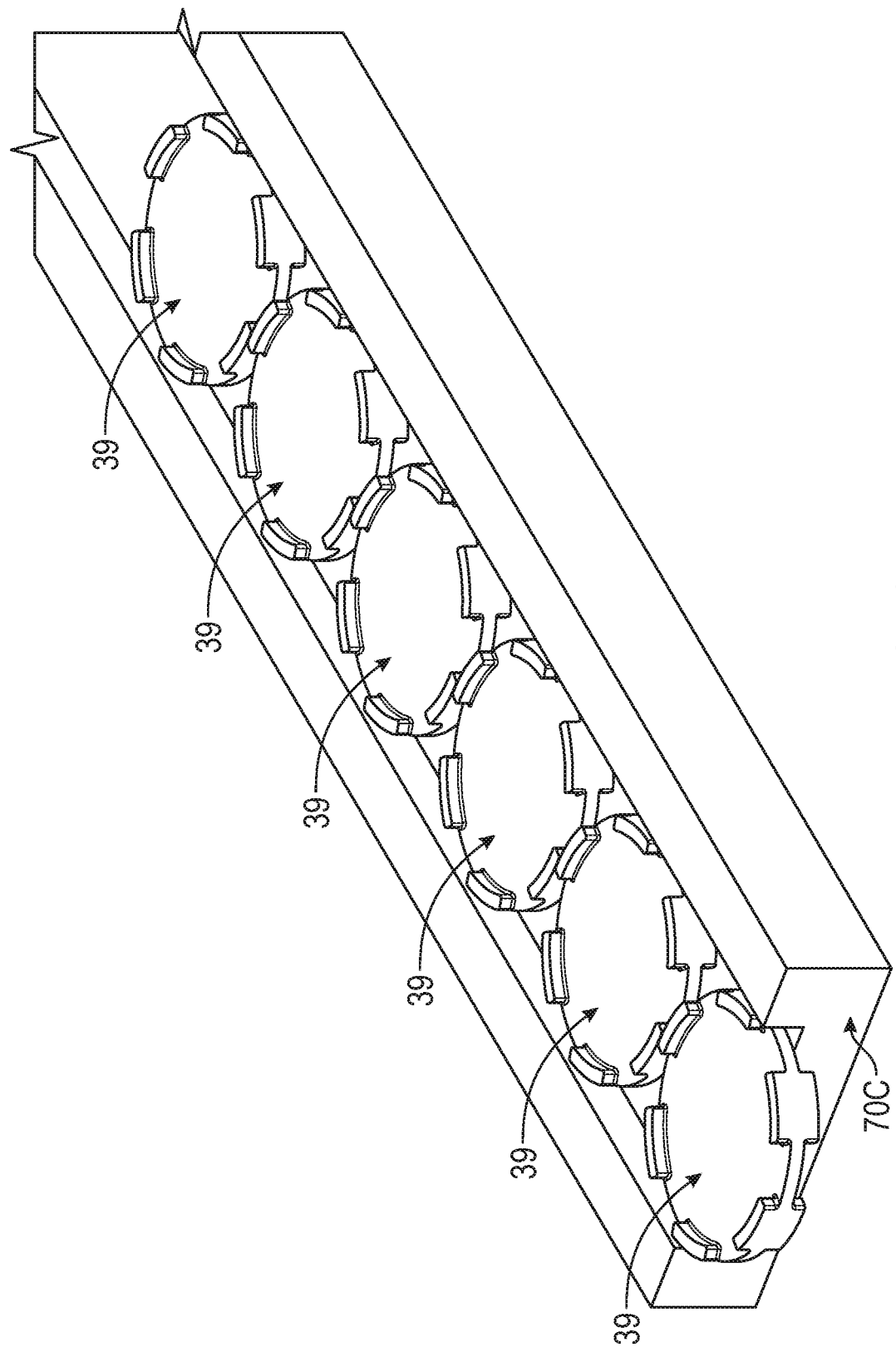
FIG. 4C is an assembly line of the valve member of the check valve of FIG. 4 in accordance with some embodiments.

FIG. 3 is a perspective view of a check valve 300, in accordance with some embodiments of the present disclosure. FIG. 4A is an exploded perspective view of the check valve 300 of FIG. 3, in accordance with some embodiments of the present disclosure. FIG. 4B is an exploded cross-sectional view of the check 300 valve of FIG. 3, in accordance with some embodiments of the present disclosure. FIG. 4C illustrates an assembly line of the valve member 39 of the check valve of FIG. 4 in accordance with some embodiments.

Referring to FIG. 3, a top portion of the check valve 300 (i.e., an upper housing 13) is displayed in cross-sectional view to more clearly illustrate some of the features of the check valve 300. Referring to FIGS. 3-4B, similar to the embodiments of FIGS. 1A and 2A, the check valve 300 includes an axially extending body 301 defining a central longitudinal axis X1. The body 301 may be a generally cylindrical (or tubular) structure and may include an upper housing 13 and a lower housing 17. The upper housing 13 may include a first end portion 29 and an axially opposite second end portion 31. As illustrated, a radial extent of the upper housing 11 at the second end portion 31 may be greater than the radial extent thereof at the first end portion 29. The lower housing 17 may include an upstream internal surface 52, and the second end portion 31 and the upstream internal surface 52 of the lower housing 17 may axially contact each other to co-operatively form a cavity 30 of the check valve 300.

The upper housing 13 may include an inlet 20 of the check valve 300 at the first end 19, and the lower housing 17 may include an outlet 25 of the check valve 300. Similar to the embodiments of FIG. 1A, the body 201 may define an internal flow passage 85 axially extending between the inlet 20 and the outlet 25 and in fluid communication therewith. As is understood, the check valve 300 may permit fluid to flow from the inlet 20 to the outlet 25, and minimize or otherwise limit, fluid flow from the outlet 25 to the inlet 20. As depicted, the upper housing 13 and the lower housing 17 may define the cavity 30 for fluidly connecting the inlet 20 and the outlet 25. In the depicted embodiments the flexible valve member 39 may be mounted in the cavity 30 to selectively permit fluid flow from the inlet 20 to the outlet 25, and prevent fluid backflow (reverse flow) from the outlet 25 to the inlet 20.

In accordance with some embodiments, the valve member 39 may be similar in structure to the valve member 37, with the exception that the valve member 39 excludes the valve stem portion 18. Thus, similar to the valve member 37, the valve member 39 may have a plurality of longitudinally extending feet 24 at an outer circumferential perimeter 23 of the valve body 22. As described above, the feet 24 may be disposed around the outer circumferential perimeter 23 of the valve body 22 in manner resembling that of a castle, and therefore may be referred to herein as castellated feet 42. The castellated feet 24 may each extend longitudinally from the outer circumferential perimeter 23 of the valve body 22. Since the castellated feet 24 of the valve member 37 are identical to the castellated feet 24 of the valve member 39 and a detailed description of the castellated feet 24 was provided with respect to the valve member 37, a detailed description thereof shall be omitted with respect to the valve member 39.

In the depicted embodiments, the valve member 39 may be mounted on a support portion 34 of the lower housing 17. The configuration of the valve member 39 with the plurality of castellated teeth 24 may provide similar manufacturing and assembly advantages as the valve member 37 of FIGS. 2A-2C. In particular, benefits are realized in the geometry of the valve members 39 in that the castellated feet 24 prevent or obstruct contacting of the upper and/or lower surfaces 22A, 22B of the valve bodies 22 during bulk packaging, assembly and/or transportation. For example, as illustrated in FIG. 4C, the valve members 39 can now be fed along a track 70C with reduced surface area for sticking and/or friction. In particular, as described above with respect to the valve member 37, the configuration of the valve members 39 in which the upper surface 24A of each of the castellated feet 24 protrudes and is thus raised above the upper surface 22A of the valve body 22 further limits the exposed surface area of the lower surfaces 22A from contacting and sticking to each other. Similarly, the configuration of the valve members 39 in which the lower surface 24B of each of the castellated feet 24 protrudes below the lower surface 22B of the valve body 22 further limits the exposed surface area of the lower surfaces 22B from contacting and sticking to each other. Thus, the probability for sticking of the valve members 39 to occur is much lower than conventional valve members as the castellated feet will keep surfaces of the bodies 22 apart at least in part. In some embodiments, the exposed surface area of the valve members 39 available for sticking is reduced by up to 69%. As can be appreciated, the degree of reduction of the exposed surface area of the valve members 39 that is available for sticking may vary accordingly based on the size and geometry of the castellated feet 24.

Additional benefits are realized in that due to the longitudinally protruding structure of the castellated feet 24, the valve member 39 is capable of being maintained concentrically in the cavity 30 of the check valve 300 when the valve member 39 experiences a back pressure condition. Furthermore, because the valve member 39 is symmetrically shaped it can be assembled on either side thereof. In all other respects, the valve member 39 may be identical to the valve member 37 described above with respect to FIG. 2B.

In accordance with some embodiments, the check valve 300 may further include a filter member 26 coupled, attached or otherwise bonded to an inner surface, e.g., surface 59 of the upper housing 13. For example, the filter member 26 may be coupled, attached or otherwise bonded through any appropriate methods including, but not limited to ultrasonic welding, heat sealing, insert molding, gluing or other attachment methods. The filter member 26 may be disposed upstream of, and spaced apart from the valve member 37. As depicted, the filter member 26 may be coupled or otherwise attached to a ledge 53 of an internal surface 55 of the upper housing 13. The filter member 26 may be configured to restrict and minimize passage of undesirable matter in the fluid flowing through the check valve 300.

The filter member 26 may be formed of a porous material capable of preventing particulate matter of a particular size from passing through and potentially reaching and causing failure of the valve member 37. For example, the filter member 26 may be formed of a porous plastic material. Alternatively, the filter member 26 may be made of a non-woven cast material, a cork material, or any other porous fabric or material. The filter member 26 may be formed with a plurality of small holes or it may be woven, to provide pores of about 20 to 200 microns in size. In some embodiments, filter member 26 may be a flexible material such as a metal or polymeric material. In some embodiments, the filter member 40 may be formed of a material capable of withstanding or filtering flow rates of between 3 to 8 liters per hour. Additionally, the filter member 26 may be formed of a porous material capable of withstanding backpressures resulting from reverse flow of up to 200 KPa. Advantageously, the latter configuration may minimize the possibility of the filter member 26 collapsing under the backpressure resulting from reverse fluid flow.

In accordance with some embodiments, the upper housing 13 may include at least one longitudinally extending rib 45 that protrudes radially inward from the upstream internal surface 57. The at least one longitudinally extending rib 45 may be configured as a protruding surface which is disposed directly above or upstream of the filter member 26. In some embodiments, the filter member 26 may be disposed between the plurality of longitudinally extending ribs 45 and the flexible valve member 39. As depicted, the filter member 26 is positioned spaced apart from and disposed with a gap G between the filter member 26 and distal ends 51 of the plurality of ribs 45. The aforementioned configuration is advantageous to maximize surface area for fluid flow from the inlet into the cavity and to minimize obstruction of fluid flow from the inlet 20 to the outlet 25.

Figure 5:
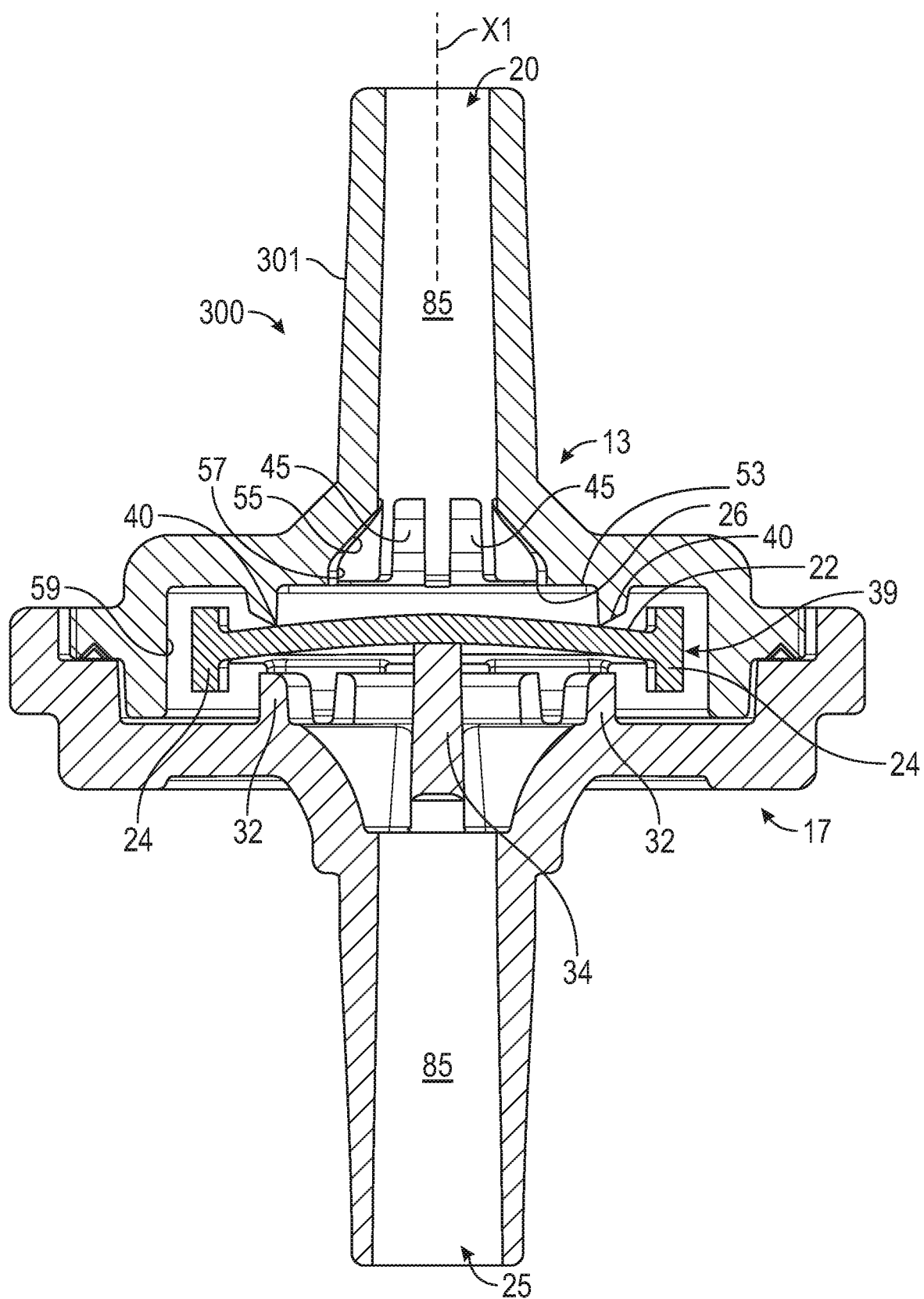
FIG. 5 is a cross-sectional view of the check valve of FIG. 3 in the closed state, wherein the check valve restricts fluid flow in the reverse directions, in accordance with some embodiments of the present disclosure.
Figure 6:
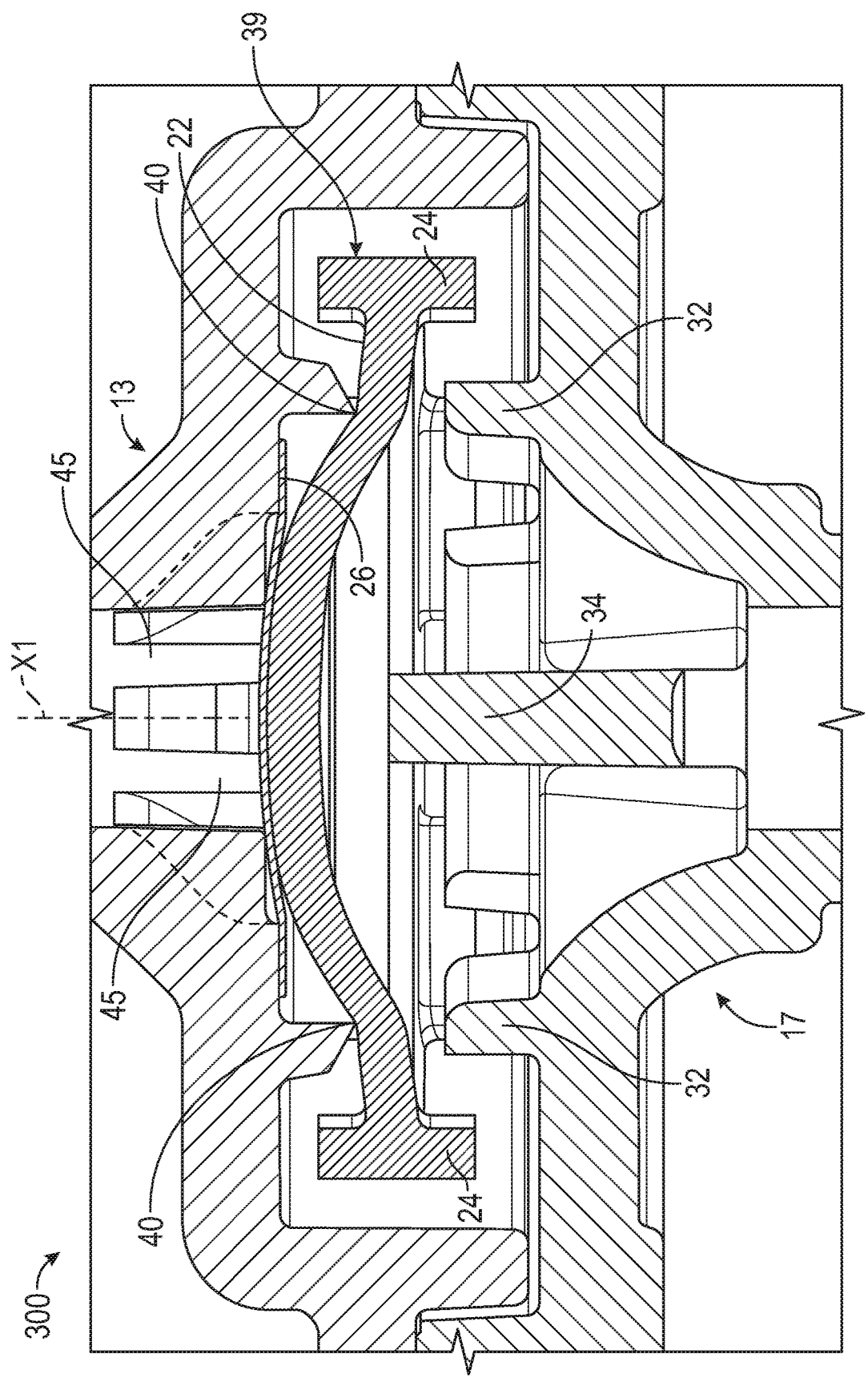
FIG. 6 is an enlarged partial cross-sectional view of the check valve of FIG. 3 in the closed state, wherein the check valve is subjected to an excessive backpressure, in accordance with some embodiments of the present disclosure.

FIGS. 5-8 are cross-sectional views of check valve 300, in accordance with some embodiments of the present disclosure. FIG. 5 is a cross-sectional view of the check valve of FIG. 3 in the closed state, wherein the check valve restricts fluid flow in the reverse directions, in accordance with some embodiments of the present disclosure. As depicted, the upper housing 13 may include the internal surface 55 extending along the length of the interior of the upper housing 13 and defining the flow passage 85. The internal surface 55 may include the upstream internal surface 57 and the downstream internal surface 59. The cavity 30 may be at least partially defined by the downstream internal surface 59 of the upper housing 13. In the depicted embodiments, the downstream internal surface 59 extends radially outward from the upstream internal surface 57. The downstream internal surface 59 may include a projection 40 which extends circularly about the central longitudinal axis X1 of the body 301 and into the cavity 30. In some embodiments, the projection 40 defines a sealing surface 42 at a distal end thereof. The projection 40 and therefore the sealing surface 42 may be disposed like a ring above the valve member 39. As illustrated in FIGS. 5 and 6, in the normally-closed state of the check valve 300, the valve member 39 contacts the sealing surface 42. Because the valve member 39 contacts the sealing surface 42, reverse flow (backflow) of fluid from the outlet 25 to the inlet 20 is prevented.

During operation, when a downstream pressure (i.e., a pressure applied by a fluid flowing from the outlet 25 to the inlet 20 is applied to the valve member 39, the valve member 39 may deflect towards the sealing surface 42 to block the fluid communication between the inlet 20 and the cavity 30, thereby restricting backflow of the fluid from the outlet 25 to the inlet 20. Preventing backflow of the fluid is advantageous in that it restricts undesirable particulate matter, for example, contained in a drug dispensed from a secondary path from flowing back through the check valve 300, thereby preventing the patient from receiving the proper drug dosage concentration or from timely delivery of the drug.

FIG. 6 is an enlarged partial cross-sectional view of the check valve of FIG. 3 in the closed state, wherein the check valve is subjected to an excessive backpressure, in accordance with some embodiments of the present disclosure. For example, an excessive back pressure exerted on the valve member 39 may cause the valve member to deflect or bend to such an extent that it abuts the filter member 26, and exerts an upward force on the filter member 26. When the valve member 39 is subjected to an excessive backpressure as illustrated in FIG. 6, the plurality of longitudinally extending ribs 45 are advantageously configured to support the valve member 39 and limit the extent to which the valve member 39 stretches the filter member 26 when the valve member 39 is subjected to excessive back pressure. To this effect, the plurality of longitudinally extending ribs 45 prevent the valve member 39 from bowing to an extent where the valve member 39 overstretches and plastically deforms or otherwise damages the filter member 26. The plurality of longitudinally extending ribs 45 thus act as a support member for the valve member 39 in the case of an excessive backflow so that it is not necessary for the filter member 26 to support the valve member 39 during excessive backflow. Thus, the plurality of longitudinally extending ribs 45 also function advantageously to prevent the filter member 39 from being displaced upwards into the inlet 20 when excessive back pressures are experienced in the check valve 300. Due to the presence of the longitudinally extending ribs 45, the filter member 26 is prevented from being displaced upwards and into the inlet 20 as a result of the force exerted by the deflected valve member 39.

Figure 7:
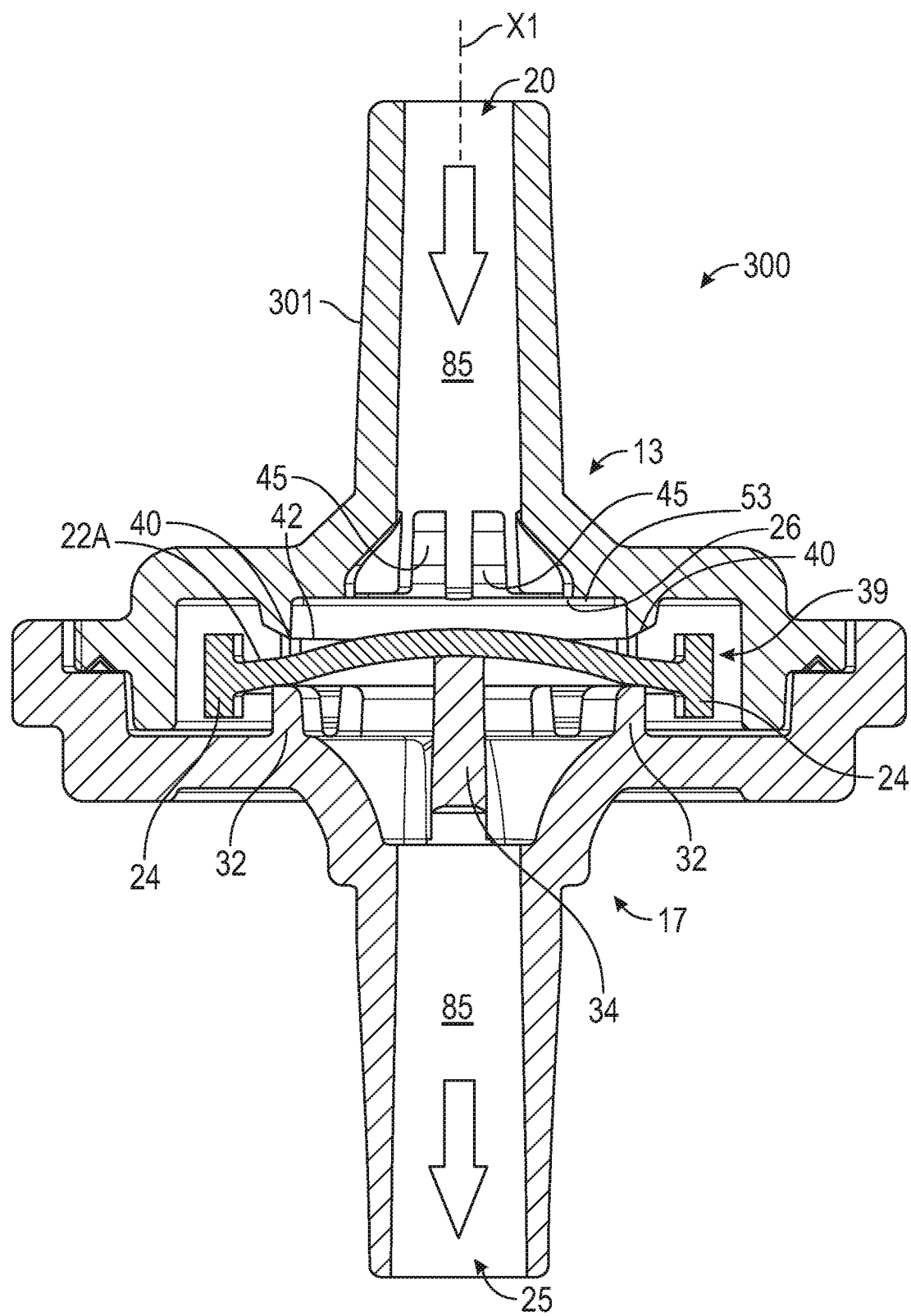
FIG. 7 is a cross-sectional view of the check valve of FIG. 3 in the open state when subjected to an upstream pressure, where the check valve permits fluid flow in the forward direction, in accordance with some embodiments of the present disclosure.
Figure 8:
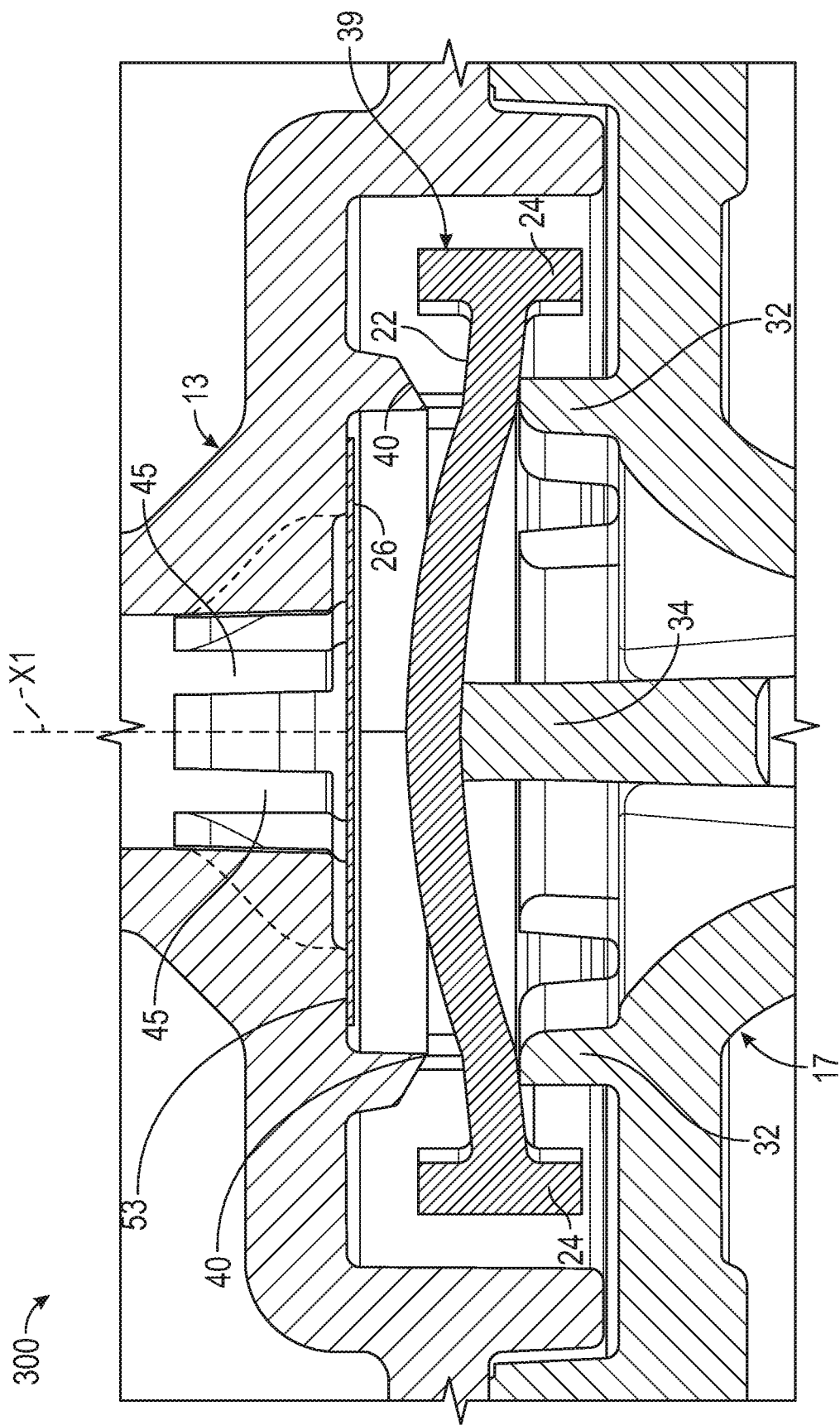
FIG. 8 is an enlarged partial cross-sectional view of the check valve of FIG. 3 in the open state when subjected to an upstream pressure, where the check valve permits fluid flow in the forward direction, in accordance with some embodiments of the present disclosure.

FIG. 7 is a cross-sectional view of the check valve 300 of FIG. 3 in the open state when subjected to an upstream pressure, where the check valve 300 permits fluid flow in the forward direction, in accordance with some embodiments of the present disclosure. FIG. 8 is an enlarged partial cross-sectional view of the check valve 300 of FIG. 3 in the open state when subjected to an upstream pressure, where the check valve 300 permits fluid flow in the forward direction, in accordance with some embodiments of the present disclosure.

As depicted, during operation, fluid may enter the check valve 300 via the inlet 20, and flow through the filter member 26 where it is filtered to trap the undesirable particulate matter, and into the cavity 30. Any grit or other undesirable particulate matter larger in size than the pores of the filter member 26 may be trapped in the filter member 40, and prevented from passing downstream to the valve member 39. The upstream pressure (i.e., pressure applied by fluid flowing from the inlet 20 to the outlet 25) applied to the valve member 39 causes the valve member 39 to bow or bend downwards at the outer edges thereof and deflect away from the sealing surface 42. Thus, the check valve is shifted from the closed state to an open state where the inlet 20, the cavity 30, and the outlet 25 are fluidly communicated. In the open state, a gap may be created between the sealing surface 42 and the upper surface 22A of the valve member 35 to allow the filtered fluid to flow therethrough. The filtered fluid may then flow through the gap, into the cavity 30, and exit the check valve 100 via the outlet 25 in the lower housing 17.

The configuration in which the filter member 40 is positioned upstream of the valve member is advantageous in that it prevents passage of undesirable particulate matter to the valve member 35 which could otherwise cause damage or wear to the valve member. The aforementioned configuration also prevents the undesirable particulate matter from potentially becoming lodged between the valve member 40 and the sealing surface 70, thereby preventing the valve member 35 from fully closing and sealing against reverse flow (backflow).

In contrast, in a conventional check valve configuration which does not include an integrated filter member, during low flow conditions, pressure exerted on the check valve as a result of the fluid flow may not be sufficient to fully open the check valve (e.g., to deflect the valve member 35) such that grit (or other undesirable particulate matter) may pass through the gap. In such conditions, the grit may get lodged in the gap and the valve may not completely close. This undesirably causes the check valve to "weep," and allow fluid to flow through the valve in the reverse direction, thereby making the check valve ineffective.

Figure 9A:
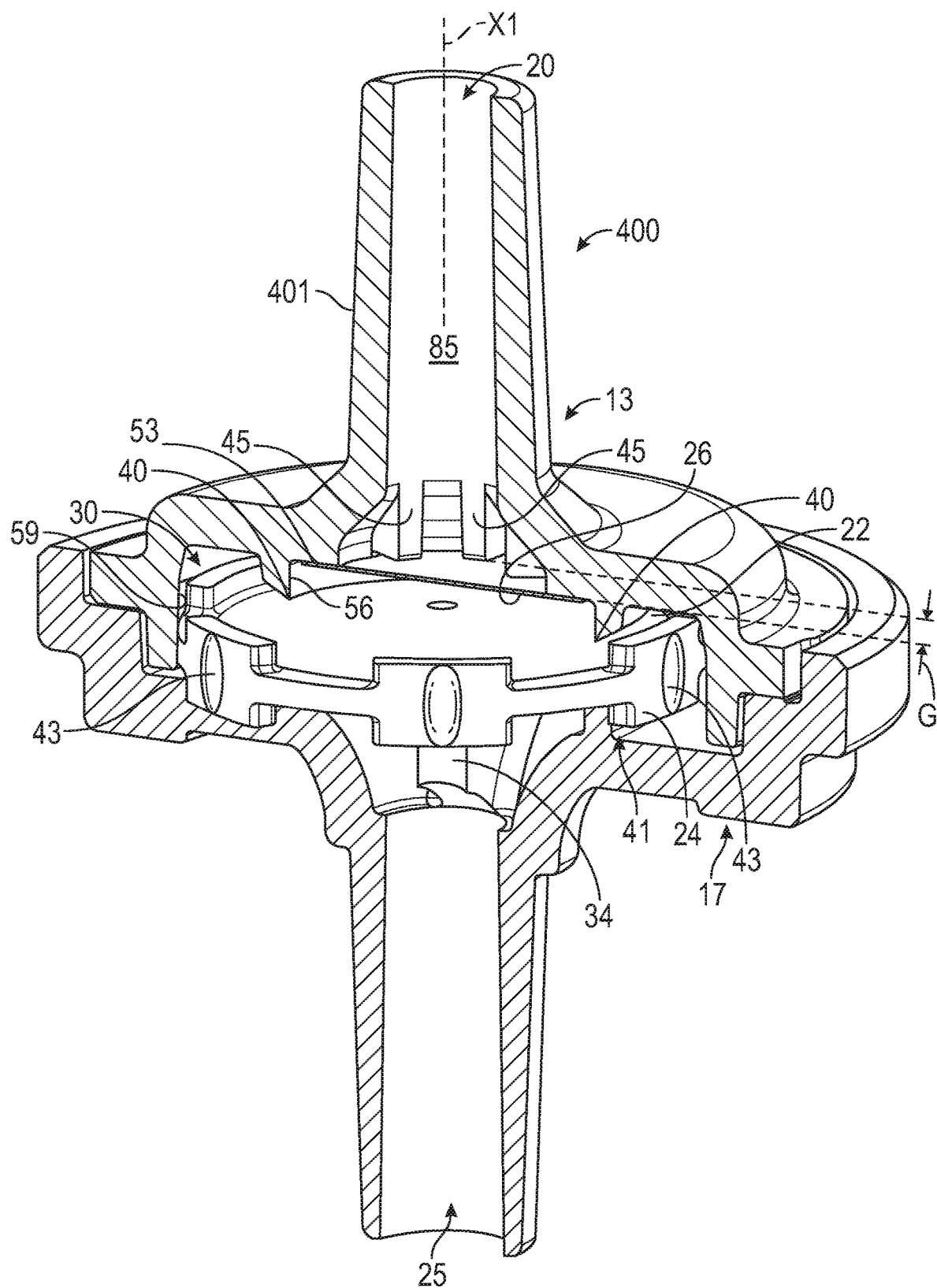
FIG. 9A is a perspective view of a check valve, in accordance with some embodiments of the present disclosure.

FIG. 9A is a perspective view of a check valve 400, in accordance with some embodiments of the present disclosure. As depicted, a top portion of the check valve 400 (i.e., an upper housing 13) is displayed in cross-sectional view to more clearly illustrate some of the features of the check valve 400. Similar to the check valve 300 of FIGS. 3 and 5, the check valve 400 includes an axially extending body 401 defining a central longitudinal axis X1. The body 401 may be a generally cylindrical (or tubular) structure and may include an upper housing 13 and a lower housing 17. In accordance with some embodiments, the upper and lower housings 13 and 17 are similar in structure to the upper and lower housings 13 and 17 of the check valve 300, thus a detailed description thereof shall be omitted with respect to the check valve 400.

In accordance with some embodiments, the valve member 41 may be similar in structure to the valve member 39, with the exception that the valve member 41 includes an additional friction rib 43 not present in valve member 39. Thus, similar to the valve member 39, the valve member 41 may have a plurality of longitudinally extending feet 24 at an outer circumferential perimeter 23 of the valve body 22. As described above, the feet 24 may be disposed around the outer circumferential perimeter 23 of the valve body 22 in manner resembling that of a castle, and therefore may be referred to herein as castellated feet 24. The castellated feet 24 may each extend longitudinally from the outer circumferential perimeter 23 of the valve body 22. Since a detailed description of the castellated feet 24 was provided with respect to the valve member 37, a detailed description thereof shall be omitted with respect to the valve member 41.

In the depicted embodiments, the valve member 41 may be mounted on a support portion 34 of the lower housing 17. The configuration of the valve member 41 with the plurality of castellated feet 24 may provide similar manufacturing and assembly advantages as the valve member 39 of FIGS. 3-8. In particular, as previously discussed with respect to valve members 37 and 39, benefits are realized in the geometry of the valve members 41 in that the castellated feet 24 prevent or obstruct contacting of the upper and/or lower surfaces 22A, 22B of the valve bodies 22 during assembly and/or transportation. In particular, as described above with respect to the valve members 37 and 39, the configuration of the valve members 41 in which the upper surface 24A of each of the castellated feet 24 protrudes and is thus raised above the upper surface 22A of the valve body 22 further limits the exposed surface area of the lower surfaces 22A from contacting and sticking to each other. Similarly, the configuration of the valve members 41 in which the lower surface 24B of each of the castellated feet 24 protrudes below the lower surface 22B of the valve body 22 further limits the exposed surface area of the lower surfaces 22B from contacting and sticking to each other. Thus, the probability for sticking of the valve members 41 to occur is much lower than conventional valve members as the castellated feet 24 will keep surfaces of the bodies 22 apart at least in part. In some embodiments, the exposed surface area of the valve members 41 available for sticking is reduced by up to 69%. As can be appreciated, the degree of reduction of the exposed surface area of the valve members 41 that is available for sticking may vary accordingly based on the size and geometry of the castellated feet 24.

Additional benefits are realized in that due to the longitudinally protruding structure of the castellated feet 24, the valve member 41 is capable of being maintained concentrically in the cavity 30 of the check valve 400 when the valve member 41 experiences a back pressure condition. Furthermore, because the valve member 41 is symmetrically shaped it can be assembled on either side thereof. In all other respects, the valve member 41 may be identical to the valve member 39 described above with respect to FIGS. 3-8.

In accordance with some embodiments, the valve members 35, 37, 39, and 41 may be formed of a flexible, resilient material which is fluid impervious. For example, the valve members 35, 37, 39, and 41 may be made of a silicon material. In other embodiments, however, the valve members 35, 37, 39, and 41 may be formed of any non-sticking, resilient material such as natural or synthetic rubber or plastic. The valve members 35, 37, 39, and 41 may be formed of a material having a shore hardness of 70 or less.

In some embodiments, the valve members 35, 37, 39, and 41 are not limited to any particular shape or size. In the depicted embodiments, however, the size of the valve members 35, 37, 39, and 41 may be limited based on desired deflection/bending characteristics of the valve members valve members 35, 37, 39, and 41 when subjected to either of the upstream or downstream forces. For example, the valve members 35, 37, 39, and 41 may be sized and shaped so as to flex or bend under fluid pressure to permit forward flow (from the inlet 20 to the outlet 25) of the fluid into the cavity 30, and to limit fluid flow in the reverse direction.

In accordance with some embodiments, the check valve 400 may further include a filter member 26 coupled, attached or otherwise bonded to an inner surface, e.g., surface 59 of the upper housing 13. Since a detailed description of the filter member 26, how it functions, and how it may be coupled, attached or otherwise bonded to the upper housing 13 was provided with respect to the valve members 37, a detailed description thereof shall be omitted with respect to the valve member 41.

Figure 9B:
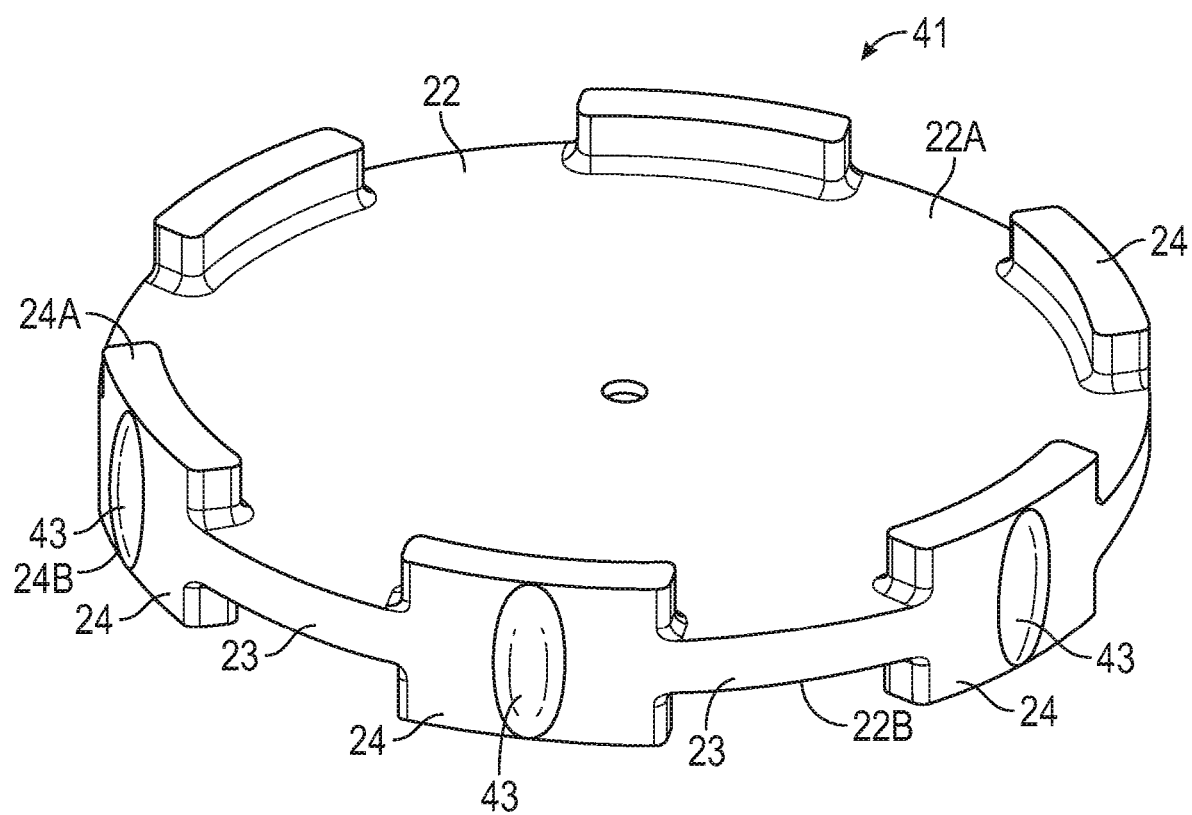
FIG. 9B is a perspective view of a valve member of the check valve of FIG. 9A, in accordance with some embodiments of the present disclosure.

FIG. 9B is a perspective view of a valve member 41 of the check valve 400 of FIG. 9A, in accordance with some embodiments of the present disclosure. As depicted, at least one of the castellated feet 24 of the valve member 41 includes a curved friction rib 43 extending radially outward from an outer surface of the castellated foot 24. The curved shape of the friction rib 43 may be advantageous over other rib shapes, for example a rib having a flatter or straighter shape because the curved shape or profile allows for reduced friction of the curved rib 43 with the downstream internal surface 59 as compared to a flat-shaped rib. The friction rib 43 may have a structure and/or be made of a may be formed of a flexible, resilient material which is capable of dampening or otherwise reducing a force, e.g., a friction force between the friction rib 43 and the downstream internal surface 59 of the upper housing 13. For example, the friction rib 43 may be made of a silicon material. In other embodiments, however, the friction rib 43 may be formed of any non-sticking, resilient material such as natural or synthetic rubber or plastic. The aforementioned configuration of the valve member 41 with the friction ribs 43 is advantageous in that in the event that the valve member 41 becomes offset from its mounting position in the cavity 30 to the point where it contacts the downstream internal surface 59, only the friction ribs 43 which protrude radially outward a greater extent than the castellated feet would contact downstream internal surface 59. Thus, a surface area of the valve member 41 which contacts the downstream internal surface 59 is drastically reduced. Accordingly, a reduced surface area of the valve member 41 contacting the downstream internal surface 59 leads to reduced friction forces between the valve member and the upper housing as compared to a conventional valve member without the outward protruding friction ribs 43.

Figure 10C:
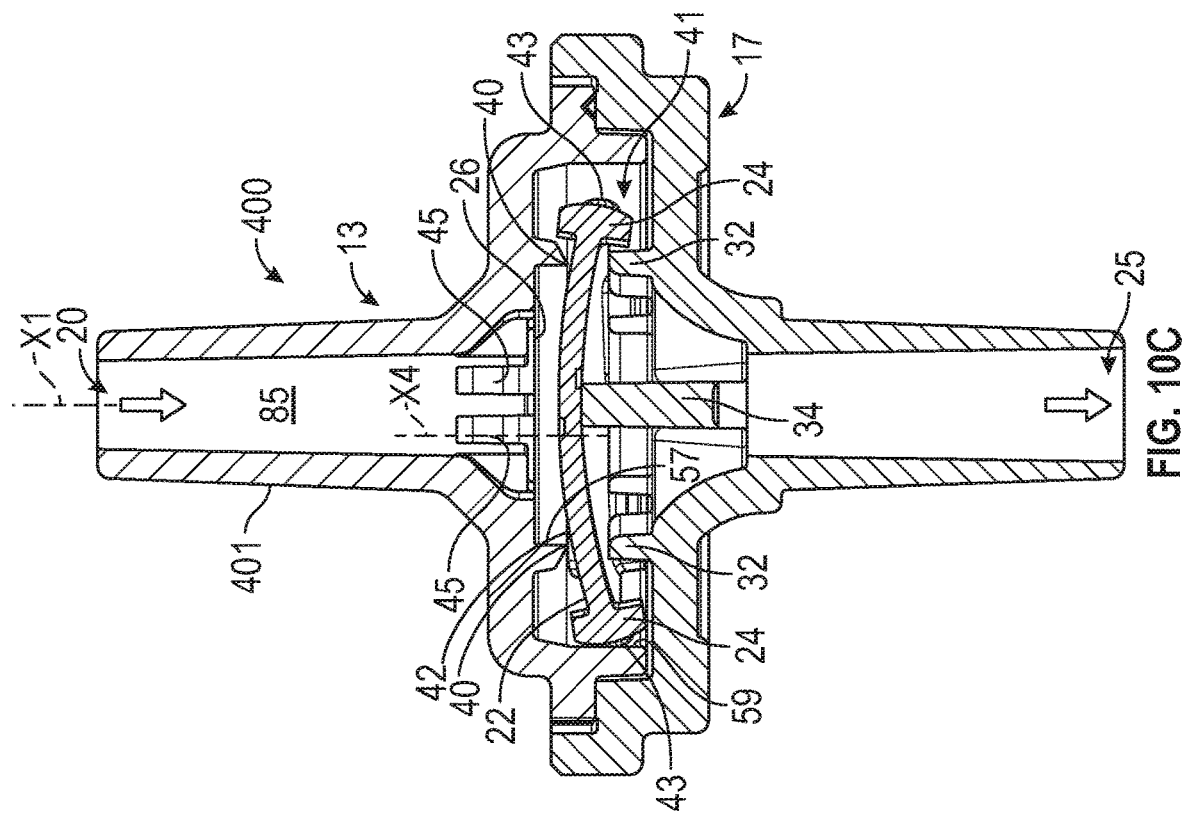
FIG. 10C is a cross-sectional view of the check valve of FIG. 9A in the open state, wherein the central axis of the valve member of FIG. 9B is misaligned with the central axis of the check valve, in accordance with some embodiments of the present disclosure.
Figure 10A:
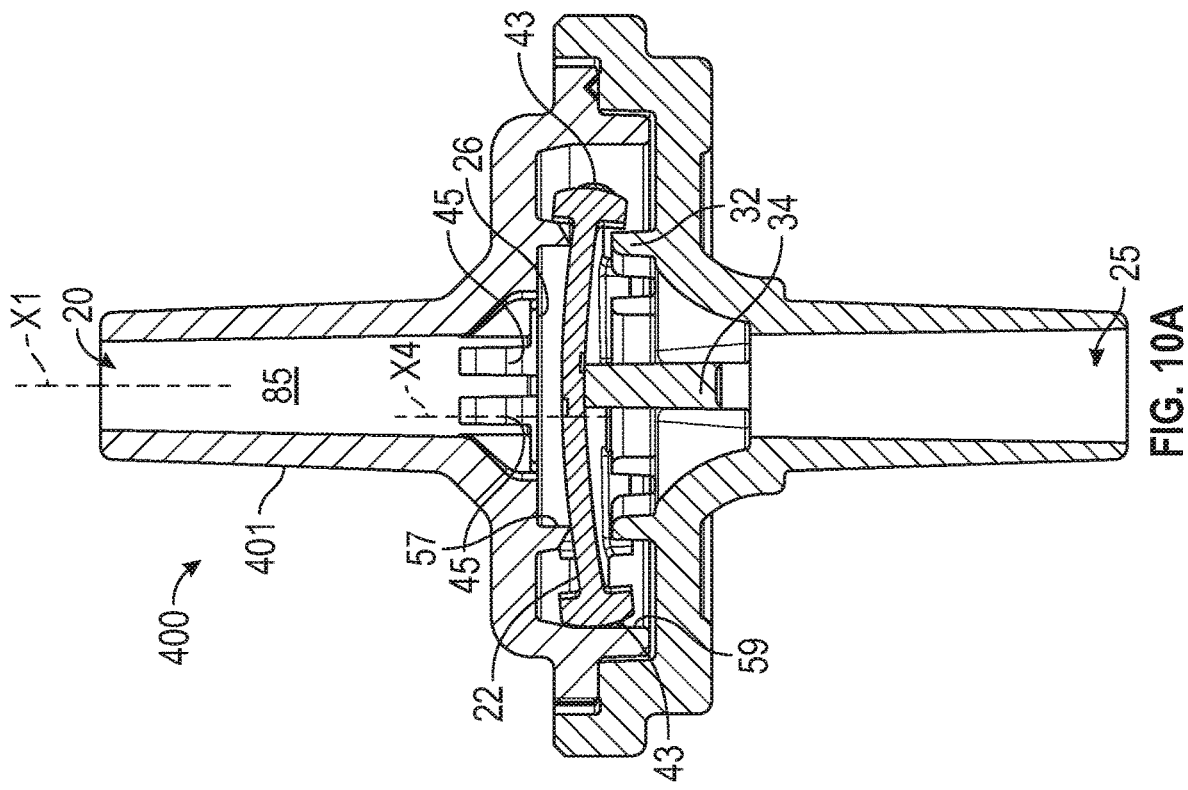
FIG. 10A is a cross-sectional view of the check valve of FIG. 9A in the closed state, wherein a central axis of the valve member of FIG. 9B is misaligned with a central axis of the check valve, in accordance with some embodiments of the present disclosure.
Figure 10B:
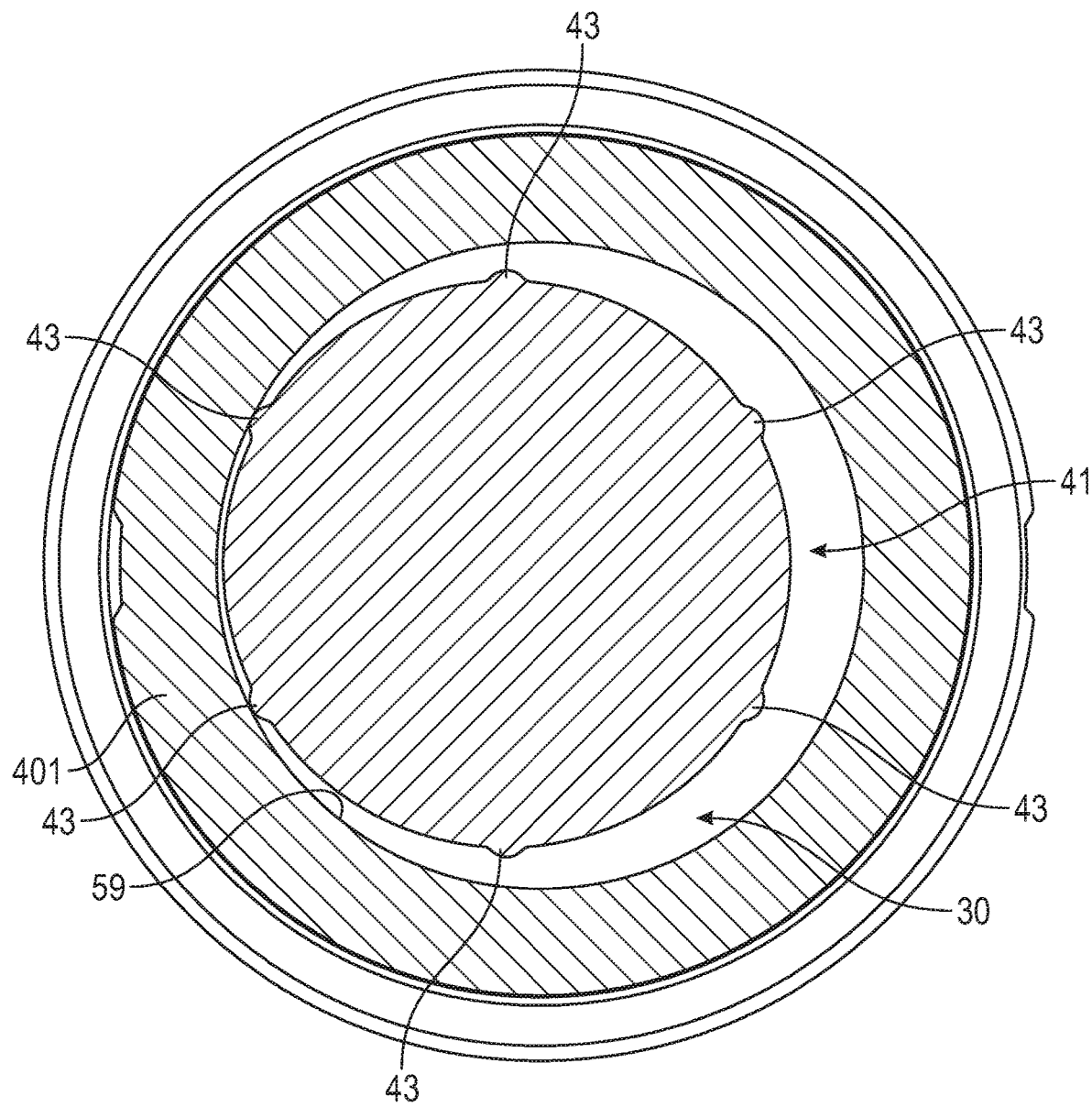
FIG. 10B is a cross-sectional view of the valve member of FIG. 9B misaligned with the central axis of the check valve, in accordance with some embodiments of the present disclosure.

FIG. 10A is a cross-sectional view of the check valve 400 of FIG. 9A in a closed state, wherein a central axis X4 of the valve member 41 of FIG. 9B is misaligned with a central axis X1 of the check valve 400, in accordance with some embodiments of the present disclosure. FIG. 10B is a cross-sectional view of the valve member 41 of FIG. 9B misaligned with the central axis of the check valve 400, in accordance with some embodiments of the present disclosure. FIG. 10C is a cross-sectional view of the check valve 400 of FIG. 9A in an open state, wherein the central axis X4 of the valve member 41 of FIG. 9B is misaligned with the central axis X1 of the check valve 400, in accordance with some embodiments of the present disclosure.

As illustrated in FIG. 10A, in the normally-closed state of the check valve 400, the valve member 39 contacts the sealing surface 42. Because the valve member 41 contacts the sealing surface 42, reverse flow (backflow) of fluid from the outlet 25 to the inlet 20 is prevented. During operation, when a downstream pressure (i.e., a pressure applied by a fluid flowing from the outlet 25 to the inlet 20) is applied to the valve member 41, the valve member 41 may deflect towards the sealing surface 42 to block the fluid communication between the inlet 20 and the cavity 30, thereby restricting backflow of the fluid from the outlet 25 to the inlet 20.

In some embodiments, the downstream pressure applied by the fluid flowing from the outlet 25 to the inlet 20 which places check valve 400 in the closed state may cause the valve member 41 to be displaced from its mounting position on the support portion 34. In particular, a central axis X4 of the valve member 41 may be misaligned with the central longitudinal axis X1 of the check valve such that the valve member 41 contacts the downstream internal surface 59 of the upper housing 13. The aforementioned configuration of the valve member 41 with the castellated feet 24 having the curved friction ribs 43 is advantageous in that since the friction ribs 43 protrude radially outward a greater extent than an outer surface of the castellated feet 24, only the portion of the valve member 41 on which the friction ribs 43 are disposed contacts the downstream internal surface 59. Thus, as illustrated in FIG. 10B, a surface area of the valve member 41 which contacts the downstream internal surface 59 is drastically reduced as compared to a conventional valve member configuration without the friction ribs 43. The reduced surface area of the valve member 41 contacting the downstream internal surface 59 leads to reduced friction forces between the valve member 41 and the internal surface of the upper housing as compared to a conventional valve member which does not have the outward protruding friction ribs 43. For example, in some embodiments, as illustrated in FIG. 10B, the surface area of the valve member 41 which contacts the downstream internal surface 59 is based on the number of friction ribs capable of contacting the downstream internal surface 59 at a time. As depicted, since a maximum of two of the friction ribs 43 contact the downstream internal surface 59 at a time, the surface area of the valve member 41 which contacts the downstream internal surface 59 is limited to the surface area of the maximum two friction ribs 43 which actually contact the downstream internal surface 59 at a given time.

As illustrated in FIG. 10C, in the open state of the check valve 41, for example when subjected to an upstream pressure (i.e., a pressure applied by a fluid flowing from the inlet 20 to the outlet 25), the check valve 400 permits fluid flow in the forward direction (direction of inlet port 20 to outlet port 25). During operation, fluid may enter the check valve 400 via the inlet 20, and flow through the filter member 26 where it is filtered to trap the undesirable particulate matter, and into the cavity 30. Any grit or other undesirable particulate matter larger in size than the pores of the filter member 26 may be trapped in the filter member 40, and prevented from passing downstream to the valve member 41. The upstream pressure (i.e., pressure applied by fluid flowing from the inlet 20 to the outlet 25) applied to the valve member 41 causes the valve member 41 to bow or bend downwards at the outer edges thereof and deflect away from the sealing surface 42.

In some embodiments, the upstream pressure applied by the fluid flowing from the inlet 20 to the outlet which places check valve 400 in the open state may cause the valve member 41 to be displaced from its mounting position on the support portion 34. In particular, a central axis X4 of the valve member 41 may be misaligned with the central longitudinal axis X1 of the check valve such that the valve member 41 contacts the downstream internal surface 59 of the upper housing 13 as discussed above. The aforementioned configuration of the valve member 41 with the castellated feet 24 having the curved friction ribs 43 is advantageous in that since the friction ribs 43 protrude radially outward a greater extent than an outer surface of the castellated feet 24, when the check valve 100 is in the open state where fluid flows from the inlet 20 towards the outlet 25 and contacts the valve member 41, the valve member 41 with the curved friction ribs 43 is displaced so as to follow a radial curved trajectory path away from the downstream internal surface 59 of the upper housing 13. In this manner the curved friction ribs 43 further separate the valve member 41 from the downstream internal surface 59 of the upper housing 13. Since contact between the valve member 41 and the downstream internal surface is minimized in this way, friction between the valve member 41 and the downstream internal surface 59 of the upper housing 13 is also minimized.

Various examples of aspects of the disclosure are described as numbered clauses (1, 2, 3, etc.) for convenience. These are provided as examples and do not limit the subject technology. Identification of the figures and reference numbers are provided below merely as examples for illustrative purposes, and the clauses are not limited by those identifications.

Clause 1: A check valve, comprising: an upper housing defining an inlet of the check valve; a lower housing defining an outlet of the check valve; a cavity interposed between and defined by the upper and lower housings for fluidly connecting the inlet and the outlet; and a valve member mounted in the cavity to selectively permit fluid flow in a first direction, and prevent fluid backflow in a second direction opposite to the first direction, the valve member comprising a valve body and a valve stem portion extending axially through a central axis of the valve body.

Clause 2: The check valve of Clause 1, further comprising a plurality of feet extending longitudinally from an outer circumferential perimeter of the valve body.

Clause 3: The check valve of Clause 2, wherein adjacent pairs of the feet each define a recessed flow portion through which fluid entering the cavity flows from the upper housing into the lower housing.

Clause 4: The check valve of Clause 1, further comprising a filter member coupled to an inner surface of the upper housing, the filter member being disposed upstream of the valve member.

Clause 5: The check valve of Clause 1, wherein: the lower housing comprises a support portion disposed in the cavity at a central portion thereof, a central axis of the support portion being aligned with a central longitudinal axis of the check valve; and the valve member is configured to be mounted and supported on the support portion.

Clause 6: The check valve of Clause 1, wherein: the upper housing comprises an internal surface and an external surface, the internal surface including an upstream internal surface and a downstream internal surface; and the downstream internal surface of the upper housing includes a projection extending into the cavity, the projection being circularly disposed about a central axis of the valve member.

Clause 7: The check valve of Clause 6, wherein: a sealing surface is defined at a distal end of the projection; and in a closed state, the valve member is configured to contact the sealing surface to limit fluid flow past the sealing surface.

Clause 8: The check valve of Clause 7, wherein: when an upstream pressure is applied to the valve member, the valve member is configured to deflect away from the sealing surface to fluidly communicate the inlet and the cavity; and when a downstream pressure is applied to the valve member, the valve member is configured to deflect towards the sealing surface to block the fluid communication between the inlet and the cavity, and restrict backflow of the fluid from the outlet to the inlet.

Clause 9: A check valve, comprising: an upper housing defining an inlet of the check valve; a lower housing axially coupled to the upper housing and comprising an outlet of the check valve; a cavity interposed between and defined by the upper and lower housings for fluidly connecting the inlet and the outlet; and a flexible valve member mounted in the cavity to selectively permit fluid flow in a first direction, and prevent fluid backflow in a second direction opposite to the first direction, the flexible valve member comprising a body having a plurality of longitudinally extending feet disposed about an outer circumferential perimeter of the body.

Clause 10: The check valve of Clause 9, wherein: the upper housing comprises an internal surface and an external surface, the internal surface including an upstream internal surface and a downstream internal surface; and the upstream internal surface comprises a plurality of longitudinally extending ribs, the longitudinally extending ribs being radially spaced apart on the upstream internal surface about a central longitudinal axis of the check valve, and protruding radially inward from the upstream internal surface.

Clause 11: The check valve of Clause 10, further comprising a filter member mounted in the upper housing and disposed between the longitudinally extending ribs and the flexible valve member.

Clause 12: The check valve of Clause 11, wherein the filter member is positioned spaced apart from and disposed with a gap between the filter member and distal ends of the longitudinally extending ribs to maximize surface area for fluid flow from the inlet into the cavity.

Clause 13: The check valve of Clause 11, wherein: the downstream internal surface of the upper housing includes a projection extending into the cavity, the projection being circularly disposed about a central axis of the flexible valve member, and a distal end of the projection defining a sealing surface; and in a closed state, the valve member is configured to contact the sealing surface to limit fluid flow past the sealing surface.

Clause 14: The check valve of Clause 13, wherein: when a downstream pressure is applied to the valve member, the valve member is configured to deflect towards the sealing surface to block fluid communication between the inlet and the cavity, and restrict backflow of the fluid from the outlet to the inlet; and the longitudinally extending ribs are configured to support the valve member and to limit an extent to which the valve member stretches the filter member when the valve member is subjected to excessive back pressure.

Clause 15: The check valve of Clause 9, wherein the valve member comprises a valve body and a stem portion extending through a central axis of the valve body for supporting the valve member in the lower housing.

Clause 16: The check valve of Clause 9, wherein each of the longitudinally extending feet comprises at least one curved friction rib extending radially outward from an outer surface of a respective longitudinally extending foot of the plurality of longitudinally extending feet.

Clause 17: The check valve of Clause 16, wherein when a central axis of the valve member is misaligned with a central longitudinal axis of the check valve such that the valve member contacts an internal surface of the upper housing and the check valve is in a closed state, a surface area of contact of the valve member with the internal surface of the upper housing is limited to a surface area of the at least one friction rib contacting the internal surface.

Clause 18: The check valve of Clause 17, wherein the at least one friction rib contacting the internal surface of the upper housing comprises a maximum of two friction ribs.

Clause 19: The check valve of Clause 16, wherein when a central axis of the valve member is misaligned with a central longitudinal axis of the check valve such that the valve member contacts an internal surface of the upper housing and the check valve is in an open state with fluid flowing from the inlet towards the outlet, the curved friction ribs are displaced to follow a radial curved trajectory path away from the internal surface of the curved rib to further separate the valve from the internal surface of the upper housing.

Clause 20: A flexible valve member of a check valve, the flexible valve member comprising: a valve body; and a plurality of feet disposed about and extending longitudinally from an outer circumferential perimeter of the valve body.

Clause 21: The check valve of Clause 20, further comprising a valve stem portion extending axially through a central axis of the valve body.

Clause 22: The check valve of Clause 20, further comprising each of the feet comprises a curved friction rib extending radially outward from an outer surface of the respective foot.

The present disclosure is provided to enable any person skilled in the art to practice the various aspects described herein. The disclosure provides various examples of the subject technology, and the subject technology is not limited to these examples. Various modifications to these aspects will be readily apparent to those skilled in the art, and the generic principles defined herein may be applied to other aspects.

A reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the invention.

The word "exemplary" is used herein to mean "serving as an example or illustration." Any aspect or design described herein as "exemplary" is not necessarily to be construed as preferred or advantageous over other aspects or designs. In one aspect, various alternative configurations and operations described herein may be considered to be at least equivalent.

As used herein, the phrase "at least one of" preceding a series of items, with the term "or" to separate any of the items, modifies the list as a whole, rather than each item of the list. The phrase "at least one of" does not require selection of at least one item; rather, the phrase allows a meaning that includes at least one of any one of the items, and/or at least one of any combination of the items, and/or at least one of each of the items. By way of example, the phrase "at least one of A, B, or C" may refer to: only A, only B, or only C; or any combination of A, B, and C.

A phrase such as an "aspect" does not imply that such aspect is essential to the subject technology or that such aspect applies to all configurations of the subject technology. A disclosure relating to an aspect may apply to all configurations, or one or more configurations. An aspect may provide one or more examples. A phrase such as an aspect may refer to one or more aspects and vice versa. A phrase such as an "embodiment" does not imply that such embodiment is essential to the subject technology or that such embodiment applies to all configurations of the subject technology. A disclosure relating to an embodiment may The claims are not intended to be limited to the aspects described herein, but are to be accorded the full scope consistent with the language of the claims and to encompass all legal equivalents. Notwithstanding, none of the claims are intended to embrace subject matter that fails to satisfy the requirement of 35 U.S.C. § 101, 102, or 103, nor should they be interpreted in such a way.

What is claimed is:

1. A check valve, comprising:
an upper housing defining an inlet of the check valve;
a lower housing axially coupled to the upper housing and comprising an outlet of the check valve;
a cavity interposed between and defined by the upper housing and the lower housing for fluidly connecting the inlet and the outlet; and
a flexible valve member mounted in the cavity, and the flexible valve member comprising a body having an outer circumferential perimeter and a plurality of longitudinally extending feet extending from upper and lower surfaces of the body and forming at least a portion of the outer circumferential perimeter of the body, wherein in a first position of the flexible valve member, a central axis of the flexible valve member is axially aligned with a central longitudinal axis of the check valve, and in a second position of the flexible valve member, the flexible valve member is laterally displaced such that the central axis of the flexible valve member is misaligned with the central longitudinal axis of the check valve, wherein in the first position and the second position, the flexible valve member permits fluid flow in a first direction from the inlet to the outlet, and prevents fluid backflow in a second direction from the outlet to the inlet.

2. The check valve of claim 1, wherein:
the upper housing comprises an internal surface and an external surface, the internal surface including an upstream internal surface and a downstream internal surface; and
the upstream internal surface comprises a plurality of longitudinally extending ribs, the plurality of longitudinally extending ribs being radially spaced apart on the upstream internal surface about the central longitudinal axis of the check valve, and protruding radially inward from the upstream internal surface.

3. The check valve of claim 2, further comprising a filter member mounted in the upper housing and disposed between the plurality of longitudinally extending ribs and the flexible valve member.

4. The check valve of claim 3, wherein the filter member is positioned spaced apart from and disposed with a gap between the filter member and distal ends of the plurality of longitudinally extending ribs to maximize surface area for the fluid flow from the inlet into the cavity.

5. The check valve of claim 3, wherein:
the downstream internal surface of the upper housing includes a projection extending into the cavity, the projection being circularly disposed about the central axis of the flexible valve member, and a distal end of the projection defining a sealing surface; and
in a closed state, the flexible valve member is configured to contact the sealing surface to limit the fluid flow past the sealing surface.

6. The check valve of claim 5, wherein:
when a downstream pressure is applied to the flexible valve member, the flexible valve member is configured to deflect towards the sealing surface to block fluid communication between the inlet and the cavity, and restrict the fluid backflow from the outlet to the inlet; and the plurality of longitudinally extending ribs are configured to support the flexible valve member and to limit an extent to which the flexible valve member stretches the filter member when the flexible valve member is subjected to excessive back pressure.

7. The check valve of claim 1, wherein the flexible valve member comprises a stem portion extending through the central axis of the flexible valve member for supporting the flexible valve member in the lower housing.

8. The check valve of claim 1, wherein each of the plurality of longitudinally extending feet comprises at least one curved friction rib extending radially outward from an outer surface of a respective longitudinally extending foot of the plurality of longitudinally extending feet.

9. The check valve of claim 8, wherein when the central axis of the flexible valve member is misaligned with the central longitudinal axis of the check valve such that the flexible valve member contacts an internal surface of the upper housing and the check valve is in a closed state, a surface area of contact of the flexible valve member with the internal surface of the upper housing is limited to a surface area of the at least one curved friction rib contacting the internal surface.

10. The check valve of claim 9, wherein the at least one curved friction rib contacting the internal surface of the upper housing comprises a maximum of two curved friction ribs.

11. The check valve of claim 8, wherein when the central axis of the flexible valve member is misaligned with the central longitudinal axis of the check valve such that the flexible valve member contacts an internal surface of the upper housing and the check valve is in an open state with the fluid flow from the inlet to the outlet, the at least one curved friction rib is displaced to follow a radial curved trajectory path away from the internal surface of the upper housing to further separate the flexible valve member from the internal surface of the upper housing.

12. The check valve of claim 1, wherein a fluid flow path extends between the outer circumferential perimeter of the flexible valve member and an inner peripheral surface of the cavity.

* * * * *